(12) United States Patent
Rosenberg

(10) Patent No.: US 8,184,094 B2
(45) Date of Patent: *May 22, 2012

(54) PHYSICALLY REALISTIC COMPUTER SIMULATION OF MEDICAL PROCEDURES

(75) Inventor: Louis B. Rosenberg, Mountain View, CA (US)

(73) Assignee: Immersion Corporation, San Jose, CA (US)

( * ) Notice: Subject to any disclaimer, the term of this patent is extended or adjusted under 35 U.S.C. 154(b) by 340 days.

This patent is subject to a terminal disclaimer.

(21) Appl. No.: 12/537,967

(22) Filed: Aug. 7, 2009

(65) Prior Publication Data

US 2009/0299711 A1    Dec. 3, 2009

Related U.S. Application Data

(63) Continuation of application No. 11/725,958, filed on Mar. 19, 2007, now Pat. No. 7,573,461, which is a continuation of application No. 10/674,423, filed on Oct. 1, 2003, now Pat. No. 7,215,326, which is a continuation of application No. 09/996,487, filed on Nov. 27, 2001, now Pat. No. 6,654,000, which is a continuation of application No. 09/276,012, filed on Mar. 25, 1999, now Pat. No. 6,323,837, which is a continuation of application No. 08/833,502, filed on Apr. 7, 1997, now Pat. No. 6,037,927, which is a continuation of application No. 08/275,120, filed on Jul. 14, 1994, now Pat. No. 5,623,582.

(51) Int. Cl.
*G09G 5/00* (2006.01)

(52) U.S. Cl. ........................................ 345/156; 345/161

(58) Field of Classification Search .......... 345/156–158, 345/161, 184
See application file for complete search history.

(56) References Cited

U.S. PATENT DOCUMENTS

| | | | |
|---|---|---|---|
| 2,906,179 | A | 9/1959 | Bower |
| 2,972,140 | A | 2/1961 | Hirsch |
| 3,157,853 | A | 11/1964 | Hirsch |
| 3,220,121 | A | 11/1965 | Cutler |
| 3,226,846 | A | 1/1966 | Wood |
| 3,497,668 | A | 2/1970 | Hirsch |
| 3,517,446 | A | 6/1970 | Codvon et al. |

(Continued)

FOREIGN PATENT DOCUMENTS

EP    0 349 086 A1    1/1990

(Continued)

OTHER PUBLICATIONS

Bergamasco, Massimo, "Haptic Interfaces: The Study of Force and Tactile Feedback Systems," IEEE International Workshop on Robot and Human Communication, 1995, pp. 15-20.

(Continued)

*Primary Examiner* — Regina Liang
(74) *Attorney, Agent, or Firm* — Kilpatrick Townsend & Stockton LLP

(57) ABSTRACT

An apparatus for interfacing the movement of a shaft with a computer includes a support, a gimbal mechanism having two degrees of freedom, and three electromechanical transducers. When a shaft is engaged with the gimbal mechanism, it can move with three degrees of freedom in a spherical coordinate space, where each degree of freedom is sensed by one of the three transducers. A fourth transducer can be used to sense rotation of the shaft around an axis.

20 Claims, 11 Drawing Sheets

U.S. PATENT DOCUMENTS

| | | |
|---|---|---|
| 3,520,060 A | 7/1970 | Crabtree et al. |
| 3,531,868 A | 10/1970 | Stevenson |
| 3,623,064 A | 11/1971 | Kagan |
| 3,662,076 A | 5/1972 | Gordon et al. |
| 3,775,865 A | 12/1973 | Rowan |
| 3,863,098 A | 1/1975 | Mehr |
| 3,890,958 A | 6/1975 | Fister et al. |
| 3,902,687 A | 9/1975 | Hightower |
| 3,903,614 A | 9/1975 | Diamond et al. |
| 3,911,416 A | 10/1975 | Feder |
| 3,919,691 A | 11/1975 | Noll |
| 3,944,798 A | 3/1976 | Eaton |
| 4,052,981 A | 10/1977 | Bachmann |
| 4,127,752 A | 11/1978 | Lowthorp |
| 4,148,014 A | 4/1979 | Burson |
| 4,160,508 A | 7/1979 | Salisbury, Jr. |
| 4,216,467 A | 8/1980 | Colston |
| 4,227,319 A | 10/1980 | Guy et al. |
| 4,236,325 A | 12/1980 | Hall et al. |
| 4,262,549 A | 4/1981 | Schwellenbach |
| 4,321,047 A | 3/1982 | Landis |
| 4,333,070 A | 6/1982 | Barnes |
| 4,360,345 A | 11/1982 | Hon |
| 4,391,282 A | 7/1983 | Ando et al. |
| 4,398,889 A | 8/1983 | Lam et al. |
| 4,439,162 A | 3/1984 | Blaine |
| 4,444,205 A | 4/1984 | Jackson |
| 4,459,113 A | 7/1984 | Boscaro Gatti et al. |
| 4,464,117 A | 8/1984 | Foerst |
| 4,477,043 A | 10/1984 | Repperger |
| 4,477,973 A | 10/1984 | Davies |
| 4,484,191 A | 11/1984 | Vavra |
| 4,513,235 A | 4/1985 | Acklam et al. |
| 4,571,834 A | 2/1986 | Fraser et al. |
| 4,575,297 A | 3/1986 | Richter |
| 4,581,491 A | 4/1986 | Boothroyd |
| 4,593,470 A | 6/1986 | Davies |
| 4,599,070 A | 7/1986 | Hladky et al. |
| 4,632,341 A | 12/1986 | Repperger et al. |
| 4,638,798 A | 1/1987 | Shelden et al. |
| 4,642,055 A | 2/1987 | Saliterman |
| 4,653,011 A | 3/1987 | Iwano |
| 4,654,648 A | 3/1987 | Herrington et al. |
| 4,664,130 A | 5/1987 | Gracovetsky |
| 4,676,002 A | 6/1987 | Slocum |
| 4,679,331 A | 7/1987 | Koontz |
| 4,680,519 A | 7/1987 | Chand et al. |
| 4,685,464 A | 8/1987 | Goldberger et al. |
| 4,703,443 A | 10/1987 | Moriyasu |
| 4,708,656 A | 11/1987 | de Vries et al. |
| 4,713,007 A | 12/1987 | Alban |
| 4,726,772 A | 2/1988 | Amplatz |
| 4,750,487 A | 6/1988 | Zanetti |
| 4,769,763 A | 9/1988 | Trieb et al. |
| 4,771,344 A | 9/1988 | Fallcaro et al. |
| 4,773,865 A | 9/1988 | Baldwin |
| 4,787,051 A | 11/1988 | Olson |
| 4,789,340 A | 12/1988 | Zikria |
| 4,791,934 A | 12/1988 | Brunnett |
| 4,794,392 A | 12/1988 | Selinko |
| 4,800,721 A | 1/1989 | Cemenska et al. |
| 4,811,608 A | 3/1989 | Hilton |
| 4,819,195 A | 4/1989 | Bell et al. |
| 4,825,872 A | 5/1989 | Tan et al. |
| 4,839,838 A | 6/1989 | LaBiche et al. |
| 4,849,692 A | 7/1989 | Blood |
| 4,868,549 A | 9/1989 | Affinito et al. |
| 4,879,556 A | 11/1989 | Duimel |
| 4,879,668 A | 11/1989 | Cline et al. |
| 4,885,565 A | 12/1989 | Embach |
| 4,888,877 A | 12/1989 | Enderle et al. |
| 4,891,764 A | 1/1990 | McIntosh |
| 4,891,889 A | 1/1990 | Tomelleri |
| 4,896,554 A | 1/1990 | Culver |
| 4,907,970 A | 3/1990 | Meenen, Jr. |
| 4,907,973 A | 3/1990 | Hon |
| 4,930,770 A | 6/1990 | Baker |
| 4,934,694 A | 6/1990 | McIntosh |
| 4,942,545 A | 7/1990 | Sapia |
| 4,945,305 A | 7/1990 | Blood |
| 4,945,501 A | 7/1990 | Bell et al. |
| 4,961,138 A | 10/1990 | Gorniak |
| 4,962,591 A | 10/1990 | Zeller et al. |
| 4,982,504 A | 1/1991 | Soderberg et al. |
| 4,986,280 A | 1/1991 | Marcus et al. |
| 5,007,085 A | 4/1991 | Greanias et al. |
| 5,007,300 A | 4/1991 | Siva |
| 5,019,761 A | 5/1991 | Kraft |
| 5,022,384 A | 6/1991 | Freels |
| 5,022,407 A | 6/1991 | Horch et al. |
| 5,035,242 A | 7/1991 | Franklin et al. |
| 5,038,089 A | 8/1991 | Szakaly |
| 5,040,306 A | 8/1991 | McMurtry et al. |
| 5,044,956 A | 9/1991 | Behensky et al. |
| 5,047,942 A | 9/1991 | Middleton et al. |
| 5,047,952 A | 9/1991 | Kramer et al. |
| 5,050,608 A | 9/1991 | Watanabe et al. |
| 5,067,072 A | 11/1991 | Talati et al. |
| 5,072,361 A | 12/1991 | Davis et al. |
| 5,078,152 A | 1/1992 | Bond et al. |
| 5,086,401 A | 2/1992 | Glassman et al. |
| 5,088,046 A | 2/1992 | McMurtry et al. |
| 5,088,055 A | 2/1992 | Oyama |
| 5,095,303 A | 3/1992 | Clark et al. |
| 5,103,404 A | 4/1992 | McIntosh |
| 5,107,080 A | 4/1992 | Rosen |
| 5,112,228 A | 5/1992 | Zouras |
| 5,116,051 A | 5/1992 | Moncrief et al. |
| 5,121,747 A | 6/1992 | Andrews |
| 5,128,671 A | 7/1992 | Thomas, Jr. |
| 5,131,844 A | 7/1992 | Marinaccio et al. |
| 5,132,672 A | 7/1992 | Clark |
| 5,137,458 A | 8/1992 | Ungs et al. |
| 5,139,261 A | 8/1992 | Openiano |
| 5,142,506 A | 8/1992 | Edwards |
| 5,142,931 A | 9/1992 | Menahem |
| 5,143,505 A | 9/1992 | Burdea et al. |
| 5,146,566 A | 9/1992 | Hollis, Jr. et al. |
| 5,148,377 A | 9/1992 | McDonald |
| 5,149,270 A | 9/1992 | McKeown |
| 5,149,487 A | 9/1992 | McKeown |
| 5,162,713 A | 11/1992 | Mohri et al. |
| 5,165,897 A | 11/1992 | Johnson |
| 5,175,459 A | 12/1992 | Danial et al. |
| 5,181,181 A | 1/1993 | Glynn |
| 5,182,557 A | 1/1993 | Lang |
| 5,184,319 A | 2/1993 | Kramer |
| 5,185,561 A | 2/1993 | Good et al. |
| 5,186,629 A | 2/1993 | Rohen |
| 5,186,695 A | 2/1993 | Mangseth et al. |
| 5,187,874 A | 2/1993 | Takahashi et al. |
| 5,189,806 A | 3/1993 | McMurtry et al. |
| 5,193,963 A | 3/1993 | McAffee et al. |
| 5,204,824 A | 4/1993 | Fujimaki |
| 5,205,289 A | 4/1993 | Hardy et al. |
| 5,212,473 A | 5/1993 | Louis |
| 5,217,003 A | 6/1993 | Wilk |
| 5,220,260 A | 6/1993 | Schuler |
| 5,223,776 A | 6/1993 | Radke et al. |
| 5,228,356 A | 7/1993 | Chuang |
| 5,230,623 A | 7/1993 | Guthrie et al. |
| 5,240,417 A | 8/1993 | Smithson et al. |
| 5,251,127 A | 10/1993 | Raab |
| 5,251,156 A | 10/1993 | Heier et al. |
| 5,259,120 A | 11/1993 | Chapman et al. |
| 5,271,290 A | 12/1993 | Fischer |
| 5,273,038 A | 12/1993 | Beaven |
| 5,275,174 A | 1/1994 | Cook |
| 5,275,565 A | 1/1994 | Moncrief |
| 5,280,265 A | 1/1994 | Kramer et al. |
| 5,283,970 A | 2/1994 | Aigner |
| 5,290,276 A | 3/1994 | Sewell, Jr. |
| 5,295,694 A | 3/1994 | Levin |
| 5,296,846 A | 3/1994 | Ledley |
| 5,299,810 A | 4/1994 | Pierce et al. |
| 5,309,140 A | 5/1994 | Everett, Jr. et al. |
| 5,317,336 A | 5/1994 | Hall |

| | | |
|---|---|---|
| 5,320,537 A | 6/1994 | Watson |
| 5,333,106 A | 7/1994 | Lanpher et al. |
| 5,334,017 A | 8/1994 | Lang et al. |
| 5,334,027 A | 8/1994 | Wherlock |
| 5,337,412 A | 8/1994 | Baker et al. |
| 5,338,198 A | 8/1994 | Wu et al. |
| 5,339,723 A | 8/1994 | Huitema |
| 5,351,692 A | 10/1994 | Dow et al. |
| 5,354,162 A | 10/1994 | Burdea et al. |
| 5,368,487 A | 11/1994 | Medina |
| 5,376,007 A | 12/1994 | Zirm |
| 5,379,663 A | 1/1995 | Hara |
| 5,384,460 A | 1/1995 | Tseng |
| 5,385,474 A | 1/1995 | Brindle |
| 5,389,849 A | 2/1995 | Asano et al. |
| 5,389,865 A | 2/1995 | Jacobus et al. |
| 5,391,081 A | 2/1995 | Lampotang et al. |
| 5,396,266 A | 3/1995 | Brimhall |
| 5,396,895 A | 3/1995 | Takashima et al. |
| 5,397,323 A | 3/1995 | Taylor |
| 5,402,582 A | 4/1995 | Raab |
| 5,403,191 A | 4/1995 | Tuason |
| 5,405,152 A | 4/1995 | Katanics et al. |
| 5,414,337 A | 5/1995 | Schuler |
| 5,417,210 A | 5/1995 | Funda et al. |
| 5,417,696 A | 5/1995 | Kashuba et al. |
| 5,428,748 A | 6/1995 | Davidson et al. |
| 5,429,140 A | 7/1995 | Burdea et al. |
| 5,435,729 A | 7/1995 | Hildreth et al. |
| 5,436,542 A | 7/1995 | Petelin et al. |
| 5,436,622 A | 7/1995 | Gutman et al. |
| 5,436,638 A | 7/1995 | Bolas et al. |
| 5,437,607 A | 8/1995 | Taylor |
| 5,438,529 A | 8/1995 | Rosenberg et al. |
| 5,445,166 A | 8/1995 | Taylor |
| 5,451,924 A | 9/1995 | Massimino et al. |
| 5,454,722 A | 10/1995 | Holland et al. |
| 5,459,382 A | 10/1995 | Jacobus et al. |
| 5,461,711 A | 10/1995 | Wang et al. |
| 5,466,213 A | 11/1995 | Hogan et al. |
| 5,467,763 A | 11/1995 | McMahon et al. |
| 5,482,051 A | 1/1996 | Reddy et al. |
| 5,482,472 A | 1/1996 | Garoni et al. |
| 5,483,961 A | 1/1996 | Kelly et al. |
| 5,509,810 A | 4/1996 | Schertz et al. |
| 5,510,832 A | 4/1996 | Garcia |
| 5,512,919 A | 4/1996 | Araki |
| 5,513,100 A | 4/1996 | Parker et al. |
| 5,513,992 A | 5/1996 | Refait |
| 5,518,406 A | 5/1996 | Waters |
| 5,547,382 A | 8/1996 | Yamasaki et al. |
| 5,575,761 A | 11/1996 | Hajianpour |
| 5,576,727 A | 11/1996 | Rosenberg et al. |
| 5,577,981 A | 11/1996 | Jarvik |
| 5,587,937 A | 12/1996 | Massie et al. |
| 5,589,828 A | 12/1996 | Armstrong |
| 5,598,269 A | 1/1997 | Kitaevich et al. |
| 5,609,485 A | 3/1997 | Bergman et al. |
| 5,609,560 A | 3/1997 | Ichikawa et al. |
| 5,623,582 A * | 4/1997 | Rosenberg .................... 345/161 |
| 5,629,594 A | 5/1997 | Jacobus et al. |
| 5,643,087 A | 7/1997 | Marcus et al. |
| 5,667,517 A | 9/1997 | Hooven |
| 5,676,157 A | 10/1997 | Kramer |
| 5,690,582 A | 11/1997 | Ulrich et al. |
| 5,701,140 A | 12/1997 | Rosenberg et al. |
| 5,704,791 A | 1/1998 | Gillio |
| 5,709,219 A | 1/1998 | Chen et al. |
| 5,721,566 A | 2/1998 | Rosenberg |
| 5,724,264 A | 3/1998 | Rosenberg et al. |
| 5,731,804 A | 3/1998 | Rosenberg |
| 5,734,373 A | 3/1998 | Rosenberg et al. |
| 5,739,811 A | 4/1998 | Rosenberg et al. |
| 5,742,278 A | 4/1998 | Chen et al. |
| 5,755,577 A | 5/1998 | Gillio |
| 5,766,016 A | 6/1998 | Sinclair et al. |
| 5,767,839 A | 6/1998 | Rosenberg |
| 5,769,640 A | 6/1998 | Jacobus et al. |
| 5,785,630 A | 7/1998 | Bobick et al. |
| 5,790,108 A | 8/1998 | Salcudean et al. |
| 5,805,140 A | 9/1998 | Rosenberg et al. |
| 5,808,665 A | 9/1998 | Green |
| 5,821,920 A | 10/1998 | Rosenberg et al. |
| 5,841,423 A | 11/1998 | Carroll, Jr. et al. |
| 5,880,714 A | 3/1999 | Rosenberg et al. |
| 5,882,207 A | 3/1999 | Lampotang et al. |
| 5,889,670 A | 3/1999 | Schuler et al. |
| 5,889,672 A | 3/1999 | Schuler et al. |
| 5,909,380 A | 6/1999 | Dubois et al. |
| 5,920,319 A | 7/1999 | Vining et al. |
| 5,929,846 A | 7/1999 | Rosenberg et al. |
| 5,941,710 A | 8/1999 | Lampotang et al. |
| 5,944,151 A | 8/1999 | Jakobs et al. |
| 5,950,629 A | 9/1999 | Taylor et al. |
| 5,976,156 A | 11/1999 | Taylor et al. |
| 6,004,134 A | 12/1999 | Marcus et al. |
| 6,024,576 A | 2/2000 | Bevirt et al. |
| 6,037,927 A | 3/2000 | Rosenberg |
| 6,046,727 A | 4/2000 | Rosenberg et al. |
| 6,057,828 A | 5/2000 | Rosenberg et al. |
| 6,059,506 A | 5/2000 | Kramer |
| 6,104,158 A | 8/2000 | Jacobus et al. |
| 6,111,577 A | 8/2000 | Zilles et al. |
| 6,125,337 A | 9/2000 | Rosenberg et al. |
| 6,131,097 A | 10/2000 | Peurach et al. |
| 6,154,198 A | 11/2000 | Rosenberg |
| 6,160,489 A | 12/2000 | Perry et al. |
| 6,162,190 A | 12/2000 | Kramer |
| 6,195,592 B1 | 2/2001 | Schuler et al. |
| 6,223,100 B1 | 4/2001 | Green |
| 6,246,390 B1 | 6/2001 | Rosenberg |
| 6,300,937 B1 | 10/2001 | Rosenberg |
| 6,323,837 B1 * | 11/2001 | Rosenberg .................... 345/156 |
| 6,422,941 B1 | 7/2002 | Thorner et al. |
| 6,437,771 B1 | 8/2002 | Rosenberg et al. |
| 6,758,843 B2 | 7/2004 | Jensen |
| 6,876,891 B1 | 4/2005 | Schuler et al. |
| 7,091,950 B2 | 8/2006 | Rosenberg et al. |
| 7,215,326 B2 | 5/2007 | Rosenberg |

FOREIGN PATENT DOCUMENTS

| | | |
|---|---|---|
| EP | 0571827 | 12/1993 |
| EP | 0571827 A1 | 12/1993 |
| GB | 2254911 A | 10/1992 |
| JP | H2-185278 | 7/1990 |
| JP | H4-8381 | 1/1992 |
| JP | 434610 A | 2/1992 |
| JP | H5-192449 | 8/1993 |
| JP | H7-24147 | 1/1995 |
| SU | 1124372 | 11/1984 |
| WO | 91/06935 | 5/1991 |
| WO | WO 91/06935 | 5/1991 |
| WO | WO 9400052 | 1/1994 |
| WO | WO 9426167 | 11/1994 |
| WO | WO 95/02233 | 1/1995 |
| WO | WO 9502801 | 1/1995 |
| WO | 9520787 | 8/1995 |
| WO | WO 9520787 | 8/1995 |
| WO | WO 9520788 | 9/1995 |
| WO | WO 9616397 | 5/1996 |
| WO | WO 9622591 | 7/1996 |
| WO | WO 9639944 | 12/1996 |

OTHER PUBLICATIONS

Chen, Elaine Y. et al, "Exos Slip Display Research and Development," DSC-vol. 55-1, Dynamic Systems and Control, vol. 1, 1994, pp. 265-270.

Durlach, Nathaniel I. et al., "Virtual Reality. Scientific and Technological Challenges," National Academy Press, Washington, D. C. 1995, pp. 160-205.

Jackson, K. M., "Linearity of Radio-Frequency Transducers," Med. & Biol. Eng. and Computer, Jul. 15, 1977, pp. 446-439.

Krueger et al., "The Responsive Workbench," IEEE Computer and Applications, 1994, pp. 12-14.

Langrana Noshir A. et al., "Dynamic Force Feedback in a Virtual Knee Palpation", Journal of Artificial Intelligence in Medicine, vol. 6, 1994, pp. 321-333.

Marcus, Beth A. et al, "Making VR Feel Real," In: Proceedings of SRI International Virtual Worlds Conference, Stanford Research Institute, 1991,7 pages.

Marcus, Beth A., "Haptic Feedback in Surgical Simulation," A Symposium by OCME, Medicine Meets VR, 1994,6 pages.

Satava, Richard M., "The Role of Virtual Reality in Medicine of the 21st Century", Virtual Reality Systems, vol. 1, No. 2, 1994, pp. 64-67.

Snibbe, Scott S., "Haptic Techniques for Media Control," In Proceeding of the 14th Annual ACM Symposium on User Interface Software and Technology, 2001, pp. 1-10.

Taubes, Gary, "Surgery in Cyberspace", Science News Articles Online Technology Magazine Articles, http://www.discover.com.issues/dec-94, Dec. 1994, 7 pages.

Hill, John, "Telepresence Technology in Medicine: Principals and Applications", 1998, IEEE vol. 85 No. 3, pp. 569-580.

Jackson, Bernie, "Force Feedback and Medical Simulation", IOS Press and Ohmsha, 1995, pp. 147-151.

Merril, Jonathon et al., "Virtual Heart Surgery: Trade Show and Medical Education", 1994, Virtual Reality World, pp. 55-57.

Merril, MD, Jonathan R., "Virtual Reality for Trade Shows and Individual Physician Training", 1994, Cover Talk, vol. 1, No. 3, pp. 40-44.

Merril, Gregory, "Special Issue on Virtual and Augmented Reality in Medicine", 1998, IEEE vol. 86, No. 3, 99-471-473.

Rosenberg, Louis B., "Medical Applications of Virtual Reality", 1994, Medical Applications, Immersion Corporation, Palo Alto, Calif., pp. 48-50.

Rosenberg, L. B., "Virtual Fixtures": Preceptual Overlays Enhance Operator Performance in Telepresence Tasks, SON 5485-SON 5597 part one.

Rosenberg, L.B., et al., "Commercially Visible Force Feedback Controller for Individuals with Neuromotor Disabilities", United States Air Force Armstrong Laboratory, Immersion Corporation, 1996, pp. 1-33.

Rosenberg, L. B., "Virtual Fixtures": Preceptual Overlays Enhance Operator Performance in Telepresence Tasks, SON 5598-SON 5712 part two.

Johnson, A., "Shape-memory alloy tactical feedback actuator," Phase I—Final Report, Air Force SBIR Contract F33-88-C-0541, Feb. 1 through Aug. 1, 1989, Armstrong Aerospace Medical Research Laboratory, Wright patterson Air Force Base, OH, (Aug. 1990().

Jones, L. et al., "A Perceptual Analysis of Stiffness," 79 Experimental Brain Research No. 1, pp. 151-156, (1990).

Kelley, A., "MagicMouse: Tactile and Kinesthetic Feedback in the Human-Computer Interface using an Electromagnetically Actuated Input/Output Device," Dept. of Elec. Engineering, Univ. of British Columbia, Vancouver, BC, pp. 1-27, ( 1993).

Kelley, A., et al., "On the Development of a Force-Feedback Mouse and Its Integration into a Graphical User Interface," in: Proceedings ASME Winter Annual Meeting (vol. 55 Dynamic Systems and Control No. 1), pp. 287-294, (1994).

Kelley, A., et al., "On the Development of a Force-Feedback Mouse and Its Integration into a Graphical User Interface," in: Symposium on Haptic Interfaces for Virtual Environment and teleoperator Systems, 1994 International Mechanical Engineering Congress and Exhibition, Chicago, IL, Nov. 1994.

Kim, W., et al, "A teleoperation training simulator with visual and kinesthetic force virtual reality," in: Human Vision, Visual Processing, and Digital Display III: Feb. 10-13, 1992 San Jose, California (Spie Proceedings, vol. 1666), Proc. SPIE 1666, pp. 560-569, (1992).

Minsky, M., et al., "Feeling and Seeing: Issues in Force Display," in: Proc. Symposium on Interactive 3D Graphics, Snowbird, UT, 1990, 1990 ACM 089791-351-5, pp. 235-242, 270, (1990).

Noll, A., "Man-Machine Tactile Communication," Dissertation for Polytechnic Institute of Brooklyn, Brooklyn, NY, (1971).

Noll, A., "Man-Machine Tactile," reprint of SID Journal (The Official Journal of the Society for Information Display), vol. 1, No. 2, pp. 5-11, 30, (Jul./Aug. 1972).

Patrick, N., "Design, Construction, and Testing of a Fingertip Tactile Display for Interaction with Virtual and Remote Environments," Master of Science Thesis, Massachusetts Institute of Technology, Cambridge, MA, (Aug. 1990).

Russo, M., et al., "Controlling Dissipative Magnetic Particle Brakes in Force Reflective Devices," DSC-vol. 42, Advances in Robotics, ASME 1992, pp. 63-70, (1992).

Salisbury, J., et al., "Virtual Environment Technology for Training (VETT), III-A-1-C. Haptic Interfaces," BBN Report No. 7661, prepared by the Virtual Environment and Teleoperator Research Consortium (VETREC) affiliated with MIT, pp. III-A-27-III-A-40, (Mar. 1992).

Schmult, B., et al., "Application Areas for a Force-Feedback Joystick", Department of Machine Perception Research AT&T Bell Laboratories, Holmdel, New Jersey, DSC-vol. 49, Interfaces ASME 1993, pp. 47-54, (1993).

Su, S., et al., "The Virtual Panel Architecture: A 3D Gesture Framework," in: 1993 IEEE Virtual Reality Annual International Symposium (VRAIS 1993), Sep. 18-22, 1993, Seattle, WA, pp. 387-393, (1993).

Tadros, A. "Control System Design for a Three Degree of Freedom Virtual Environment Simulator Using Motor/Brake Pair Actuators," Masters Degree Thesis, MIT Archive, Massachusetts Institute of Technology, Cambridge, MA, (Feb. 1990).

Tan, H. et al, "Human Factors for the Design of Force-Reflecting Haptic Interfaces," ASME WAM 1994, pp. 1-11.

Tan, H. et al., "Manual Resolution of Compliance When Work and Force Cues are Minimized," Advances in Robotics, Mechatronics, and Haptic Interfaces, DSC-vol. 49, ASME 1993, pp. 99-104, (1993).

Unknown Authors, "Hard Drivin' Schematic Package," Atari Games Corporation, Milpitas, CA, 1989.

Voyles, R., et al., "Design of a Modular Tactile Sensor and Actuator Based on an Electrorheological Gel," in: Proceedings of the 1996 IEEE International Conference on Robotics and Automation, Minneapolis, MN—Apr. 1996.

Yamakita, M. et al., "Tele Virtual Reality of Dynamic Mechanical Model," in: Procedings of the 1992 IEEE/RSJ Conference on Intelligent Robots and Systems, Raleigh, NC, Jul. 7-10, 1992.

Bostrom, M. et al., "Design of an Interactive Lumbar Puncture Simulator With Tactile Feedback," IEEE 0/7803-1363, pp. 280-286, (1993).

Erdman, A., et al, "Kinematic and Kinetic Analysis of the Human Wrist by Stereoscopic Instrumentation," ASME 1978 Advances in Bioengineering, p. 79082; ASME Journal of Biomechanical Engineering; vol. 101, pp. 124-133; 1979.

Marcus, B., "Hands On: Haptic Feedback in Surgical Simulation," in: Proceedings of the Medicine Meets Virtual Reality II: Interactive Technology and Healthcare: Visionary Applications for Simulation, Visualization, Robotics (Medicine Meets VR 1994), Jan. 27.

Marcus, B., "Touch Feedback in Surgery," in: Official Proceedings of the Virtual Reality and Medicine: The Cutting Edge, Sep. 8.

Patrick, "Design, Construction, and Testing of a Fingertip Tactile Display for Interaction with Virtual and Remote Environments." *Master of Science Thesis*, MIT, Aug. 1990, archived Nov. 8. 1990.

Calder, "Design of a Force-Feedback Touch-Introducing Actuator for Teleoperator Robot Control." *Bachelor of Science Thesis*, MIT, May 1983, archived Jun. 23, 1983.

Wiker, "Teletouch Display Development: Phase 1 Report." *Technical Report 1230*, Naval Ocean Systems Center, San Diego, Jul. 1988.

Bliss, "Optical-to-Tactile Image Conversion for the Blind," *IEEE Transactions on Man-Machine Systems*, vol. MMS-11, No. 1, Mar. 1970.

Johnson, "Shape-Memory Alloy Tactile Feedback Actuator." *Armstrong Aerospace Medical Research Laboratory*, AAMRL-TR-90-039, Aug. 1990.

Kontarinis et al., "Tactile Display of Vibratory Information in Teleoperation and Virtual Environments," Presence, 4(4):387-402, Harvard Univ., 1995.

Aukstakalnis et al., "Silicon Mirage: The Art and Science of Virtual Reality," ISBN 0-938151-82-7, pp. 129-180, 1992.

Eberhardt et al., "Inducing Dynamic Haptic Perception by The Hand: System Description and Some Results." DSC-vol. 55-1, *Dynamic Systems and Control*: vol. 1, ASME 1994.

Gobel et al., "Tactile Feedback Applied to Computer Mice," *International Journal of Human-Computer Interaction*, vol. 7, No. 1, pp. 1-24, 1995.

Pimentel et al., "Virtual Reality: through the new looking glass," 2nd Edition; McGraw-Hill, ISBN 0.07-050167-X, pp. 41-202, 1994.

"Cyberman Technical Specification," *Logitech Cyberman SWIFT Supplement to Logitech Mouse Technical Reference and Programming Guide*, Apr. 5, 1994.

Ouhyoung et al., "The Development of a Low-Cost Force Feedback Joystick and Its Use in the Virtual Reality Environment," *Proceedings of the Third Pacific Conference on Computer Graphics and Applications*, Pacific Graphics '95, Seoul, Korea, Aug. 21-24, 1995.

Kaczmarek et al., "Tactile Displays." *Virtual Environment Technologies*, Chap. 9, pp. 349-414.

Lake, "Cyberman from Logitech," at http://www.ibiblio.org/GameBytes/issue21/greviews/cyberman.html, 1994.

"Component Maintenance Manual With Illustrated Parts List, Coaxial Control Shaker Part No. C-25502," Safe Flight Instrument Corporation, Revised Jan. 28, 2002 (3 pages).

"Technical Manual Overhaul Instructions With Parts Breakdown, Coaxial Control Shaker Part No. C-25502," Safe Flight Instrument Corporation, Revised Jul. 15, 1980 (23 pages).

Scannell, "Taking a Joystick Ride," *Computer Currents*, Boston Edition, vol. 9. No. 11, Nov. 1994.

Yamakita et al., "Tete-Virtual Reality of Dynamic Mechanical Model," *Proceedings of the 1992 IEEE/RSJ International Conference on Intelligent Robots and Systems*, Raleigh, NC, Jul. 7-10, 1992.

Noll, "Man-Machine Tactile." *SID Journal*, Jul./Aug. 1972 Issue.

Rosenberg, "Virtual Fixtures: Perceptual Overlays Enhance Operator Performance in Telepresence Tasks," *Ph.D. Dissertation*, Stanford University, Jun. 1994.

"3D Immersion Interface Tool," Immersion Probe™, 1993.

"Immersion Probe-MDT," Immersion Human Interface Corporation.

"The Personal Digitizer™," Immersion Human Interface Corporation 1994.

"Useful Technology for Your Files," Designer's Corner, Design News, Mar. 7, 1994.

Adelstein Bernard D. et al. "A. High Performance Two Degree-of-Freedom Kinesthetic Interface," Massachusetts Institute of Technology 1992, pp. 108-112.

Adelstein Bernard D. et al., "Design and Implementation of a Force Reflecting Manipulandum for Manual Control Research," 1992, pp. 1-24.

Adelstein et al., "Design and Implementation of a Force Reflecting Manipulandum for Manual Control research." DSC-vol. 42, *Advances in Robotics*, pp. 1.12, 1992.

Adelstein, "A Virtual Environment System for the Study of Human Arm Tremor," *Ph.D. Dissertation*, Dept. of Mechanical Engineering, MIT, Jun. 1989. archived Mar. 13, 1990.

Atkinson, W. et al., "Computing with Feeling," Comput. & Graphics, vol. 2, Pergamon Press, 1977, pp. 97-103.

Baigrie, "Electric Control Loading—A Low Cost, High Performance Alternative," *Proceedings of Interservice/Industry Training Systems Conference*, pp. 247-254, Nov. 6-8, 1990.

Batter, J. et al., "Grope-I: A Computer Display to the Sense of Feel," Proc. IFIP Congress 1971. pp. 759-763.

Bejczy et al., "A Laboratory Breadboard System for Dual-Arm Teleoperation," *Soar '89 Workshop*, JSC, Houston, TX, Jul. 25-27, 1989.

Bejczy et al., "Generalization of Bilateral Force-Reflecting Control of Manipulators," *Proceedings of Fourth CISM-IFToMM*, Sep. 8-12, 1981.

Bejczy et al., "Kinesthetic Coupling Between Operator and Remote Manipulator," *International Computer Technology Conference, The American Society of Mechanical Engineers*, San Francisco, CA, Aug. 12-15, 1980.

Bejczy, "Sensors, Controls, and Man-Machine Interface for Advanced Teleoperation," *Science*, vol. 208, No. 4450, pp. 1327-1335, 1980.

Bejczy, Antal K., "The Phantom Robot: Predictive Displays for Teleoperation with Time Delay," IEEE 1990, pp. 546-550.

Bejczy, et al., "Universal Computer Control System (UCCS) for Space Telerobots," CH2413-3/87/0000/0318501.00 1987 IEEE, 1987.

Bostrom, M. et al., "Design of an Interactive Lumbar Puncture Simulator With Tactile Feedback," IEEE 0-7803-1363-1, 1993, pp. 280-286.

Brooks et al., "Hand Controllers for Teleoperation—A State-of-the-Art Technology Survey and Evaluation," *JPL Publication 85-11*, NASA-CR-175890; N85-28559, pp. 1-84, Mar. 1, 1985.

Burdea et al., "Distributed Virtual Force Feedback, Lecture Notes for Workshop on Force Display in Virtual Environments and its Application to Robotic Teleoperation," *1993 IEEE International Conference on Robotics and Automation*, pp. 25-44, May 2, 1993.

Burdea, Grigore et al., "A Portable Dextrous Master with Force Feedback," Presence: Teleoperators and Virtual Environments, MIT Press, Jun. 1991.

Burdea, Grigore et al., "Dextrous Telerobotics with Force Feedback—An Overview," Robotics 1991, vol. 9.

Burdea, Grigore et al., "Distributed Virtual Force Feedback," IEEE, May 1993, pp. 25-44.

Buttolo, Pietro et al:, "Pen-Based Force Display for Precision Manipulation in Virtual Environments," IEEE Mar. 1995, pp. 14.

Caldwell et al.. "Enhanced Tactile Feedback (Tele-Taction) Using a Multi-Functional Sensory System," 1050-4729/93, pp. 955-960, 1993.

Colgate, J. Edward et al., Implementation of Stiff Virtual Walls in Force-Reflecting Interfaces, Sep. 22, 1993, pp. 1-9.

Cover, Stephen A. et al., "Interactively Deformable Models for Surgery Simulation" IEEE Computer Graphics & Applications, pp. 68-75, Nov. 1993.

Eberhardt et al., "OMAR—A Haptic display for speech perception by deaf and deaf-blind individuals," *IEEE Virtual Reality Annual International Symposium*, Seattle, WA, Sep. 18-22, 1993.

Ellis, R.E. et al., "Design and Evaluation of a High-Performance Prototype Planar Haptic Interface," ASME Dec. 3, 1993, DSC-vol. 49, pp. 55-64.

Fischer, Patrick et al., "Specification and Design and Input Devices for Teleoperation," 1990.

Fisher, S.S. et al., "Virtual Environment Display System," ACM Interactive 3D Graphics, Oct. 1986.

Golow et al., "Controlled Impedance Test Apparatus for Studying Human Interpretation of Kinesthetic Feedback," WA11-11:00, pp. 332-337.

Hannaford, Blake et al., "Performance Evaluation of a Six-Axis Generalized Force-Reflecting Teleoperator," IEEE May/Jun. 1991, vol. 21. No. 3, pp. 620-633.

Hirota, Koichi et al., "Development of Surface Display," IEEE 0-7803-1363-1, 1993, pp. 256-262.

Hon, David, "Ixion's Realistic Medical Simulations" Virtual Reality World, Jul./Aug. 1994, pp. 59-62.

Howe, "A Forte-Reflecting Teleoperated Hand System for the Study of Tactile Sensing in Precision Manipulation," *Proceedings of the 1992 IEEE International Conference on Robotics and Automation*, Nice, France, May 1992.

Howe, R. et al., "Task Performance with a Dextrous Teleoperated Hand System," Telemanipulator Technology '92, Proceedings of SPIE, vol. 1833, Nov. 1992, pp. 1-9.

IBM Technical Disclosure Bulletin, "Mouse Ball-Actuating Device With Force and Tactile Feedback," vol. 32, No. 9B, Feb. 1990.

Iwata, "Pen-based Haptic Virtual Environment," 0-7803-1363-1/93 IEEE, pp. 287-292, 1993.

Iwata, H., "Artificial Reality with Force Feedback: Development of Desktop Virtual Space with Compact Master Manipulator," Computer Graphics, vol. 24, No. 4, 1990, pp. 165-170.

Iwata, Hiroo et al., Volume Haptization, IEEE 1993, pp. 16-18.

Jacobsen et al., "High Performance, Dextrous Telerobotic Manipulator With Force Reflection," *Intervention/ROV '91 Conference & Exposition*, Hollywood, Florida, May 21-23, 1991.

Jacobsen, S.C. et al., "High Performance, High Dexterity, Force Reflective Teleoperator II," ANS Topical Meeting on Robotics & Remote Systems, Albuquerque, New Mexico (Feb. 24-27, 1991) pp. 1-10.

Jones et al., "A perceptual analysis of stiffness," ISSN 0014-4819 Springer International (Springer-Verlag); *Experimental Brain Research*, vol. 79, No. 1, pp. 150-156, 1990.

Kilpatrick, P., "The Use of a Kinesthetic Supplement in an Interactive Graphics System," Univ. Of North Carolina, Computer Science, 1976, pp. 1-175.

Kim, Won S. et al., "A Telcoperation Training Simulator with Visual and Kinesthetic Force Virtual Reality".

Kim, Won S. et al., "Graphics Displays for Operator Aid in Telemanipulation." IEEE 1991. pp. 1059-1067.

Kontarinis et al., "Display of High-Frequency Tactile Information to Teleoperators," *Telemanipulator Technology and Space Telerobotics*, Won S. Kim. Editor, Proc. SPIE vol. 2057, pp. 40-50, Sep. 7-9, 1993.

Kotoku, T. et al., "Environrient Modeling for the Interactive Display (EMID) Used in Telerobotic Systems," IROS '91, IEEE Cat. No. 91TH0375-6, pp. 999-1004.

Kotoku, Tetsuo, "A Predictive Display with Force Feedback and its Application to Remote Manipulation System with Transmission Time Delay," Proceedings of the 1992 IEEE Int'l Conf. on Intelligent Robots and Systems, 1992, pp. 239-246.

Marcus, "Touch Feedback in Surgery," *Proceedings of Virtual Reality and Medicine the Cutting Edge*, Sep. 8-11, 1994.

McAffee et al., "Teleoperator Subsystem/Telembot Demonstrator: Force Reflecting Hand Controller Equipment Manual," *JPL* 1988, JPL D-5172.

Merril, Jonathan et al., "Cyber Surgery: Cutting Costs, Sewing Benefits" Virtual Reality Special Report, Summer 1994, pp. 39, 40 and 42.

Merril, Jonathan, et al., "Surgical Simulation Using Virtual Reality Technology: Design, Implementation, and Implications" Surgical Technology International III, pp. 53-60.

Merril, Jonathan, et al., "Virtual Reality for Trade Shows and Individual Physician Training" Medical Applications, pp. 40-44, Spring 1994.

Meyer, Kenneth et al., "A Survey of Position Trackers." The Massachusetts Institute of Technology 1992, Presence, vol. 1, No. 2.

Minsky, "Computational Haptics: The Sandpaper System for Synthesizing Texture for a Force-Feedback Display," *Ph.D. Dissertation*, MIT, Jun. 1995, archived Jul. 6, 1995.

Minsky, M. et al., "Feeling and Seeing: Issues in Force Display," Association for Computing Machinery, 1990, pp. 235-270.

Ouhyoung et al., "A Low-Cost Force Feedback Joystick and Its Use in PC Video Games," *IEEE Transactions on Consumer Electronics*, vol. 41, No. 3, Aug. 1995.

Ouh-Young, "Force Display in Molecular Docking," Doctoral Dissertation, University of North Carolina at Chapel Hill, UMI Order No. 9034744, p. 1-369, 1990.

Ouh-young, M., "Force Display in Molecular Docking," Univ. of N. Carolina, 1990, pp. 1-12, 66-85.

Ouh-young, Ming et al., "Force Display Performs Better than Visual Display in a Simple 6-D Docking Task," IEEE 1989, pp. 1462-1466.

Patrick et al., "Design and Testing of a Non-reactive, Fingertip, Tactile Display for Interaction with Remote Environments," *Cooperative Intelligent Robotics in Space*, Rui J. deFigueiredo et al, Editor, Proc. SPIE vol. 1387, pp. 215-222, 1990.

Rabinowitz et al., "Multidimensional tactile displays: Identification of vibratory intensity, frequency, and contractor area," *Journal of the Acoustical Society of America*, vol. 82. No. 4, Oct. 1987.

Rosenberg, Louis B. et al., "Perceptual Decomposition of Virtual Haptic Surfaces," IEEE, Oct. 1993.

Rosenberg, Louis B., "Perceptual Design of a Virtual Rigid Surface Contact," Center for Design Research Stanford University, Air Force Material Command. Apr. 1993, pp. 1-41.

Rosenberg, Louis B., "The Use of Virtual Fixtures as Perceptual Overlays to Enhance Operator Performance in Remote Environments," Air Force Material Command, Sep. 1992, pp. 1-42.

Rosenberg, Louis B., "Virtual Fixtures as Tools to Enhance Operator Performance in Telepresence Environments," SPIE Telemanipulator Technology, 1993.

Rosenberg, Louis B., "Virtual Haptic Overlays Enhance Performance in Telepresence Tasks," SPIE 1994.

Rosenberg, Louis B., Crew Systems Directorate Biodynamics and Biocommunications Division Wright-Patterson, Air Force Material Command, Mar. 1993, pp. 1-45.

Russo, "Controlling Dissipative Magnetic Particle Brakes in Force Reflective Devices." DSC-vol. 42, *Advances in Robotics*, pp. 63-70, ASME 1992.

Russo, "The Design and Implementation of a Three Degree of Freedom Force Output Joystick," *MIT Libraries Archives* pp. 1-131, May 1990, archived Aug. 14, 1990.

Russo, M. "The Design and Implementation of a Three Degree-of-Freedom Force Output Joystick," Dept. of Mech. Engineering, 1990.

Schmult, B. et al., "Application Areas for a Force-Feedback Joystick," DSC-vol. 49, Advances in Robotics, Mechatronics, and Haptic Interfaces, ASME 1993, pp. 47-54.

Shimoga, "Finger Force and Touch Feedback Issues in Dexterous Telemanipulation," *Proceedings of Fourth Annual Conference on Intelligent Robotic Systems for Space Exploration*, Rensselaer Polytechnic Institute, Sep.30-Oct. 1, 1992.

Smith, Geoffrey, "Call It Palpable Progress," Business Week, Oct. 9, 1995, p. 93, 96.

Snow et al., "Model-X Force-Reflecting-Hand-Controller." NT Control No. NPO-17851; JPL Case No. 7348, pp. 1-4 with 45 pages of attachments, Jun. 15, 1989.

Snow, E. et al., "Compact Force-Reflecting Hand Controller," NASA Tech Brief, vol. 15, No. 4, Item 153, Apr. 1991, pp. 1, 1-3, 1a-15a.

Stanley et al., "Computer Simulation of Interacting Dynamic Mechanical Systems Using Distributed Memory Parallel Processors," DSC-vol. 42, *Advances in Robotics*, pp. 55-61, ASME 1992.

Tadros, "Control System Design for a Three Degree of Freedom Virtual Environment Simulator Using Motor/Brake Pair Actuators," *MIT Archive*, pp. 1-88, Feb. 1990, archived Aug. 13, 1990.

Tan, H. et al., "Manual Resolution of Compliance when Work and Force Cues are Minimized," DSC-vol. 49, Advances in Robotics, Mechatronics, and Haptic Interfaces, ASME 1993, pp. 99-104.

Tan, Hong Z. et al., "Human Factors for the Design of Force-Reflecting Haptic Interfaces," Tan, Srinivasan, Eberman & Chang, ASME WAM 1994, pp. 1-11.

Terry et al., "Tactile Feedback in a Computer Mouse," *Proceedings of Fourteenth Annual Northeast Bioengineering Conference, University of New Hampshire*, Mar. 10-11, 1988.

Winey III, Calvin, "Computer Simulated Visual and Tactile Feedback as an Aid to Manipulator and Vehicle Control," MIT Dept. of Mech. Engineering, 1981, pp. 1-79.

Yamakita, M. et al., Tele-Virtual Reality of Dynamic Mechanical Model, IEEE, Jul. 7-10, 1992, pp. 1103-1110.

Adachi, Y., et al., "Sensory Evaluation of Virtual Haptic Push-Buttons," Technical Research Center, Suzuki Motor Corporation, (Nov. 1994).

Adelstein, B., "A Virtual Environment System for the Study of Human Arm Tremor," Ph.D. Dissertation, Dept. of Mechanical Engineering, MIT, (Jun. 1989).

Akamatsu, M., et al., "Multi-Modal Mouse: A Mouse type device with tactile and force display," Presence, vol. 3 No. 1, 73-80, (1994).

Atari Games Technical Publication Department, "Hard Drivin' Operator's Manual with Illustrated Parts List," Atari Games Corporation, Milpitas, CA, 1989.

Aukstakalnis, S. et al., "*Silicon Mirage: The M and Science of Virtual Reality*," Berkeley, CA, Peach Pit Press, pp. 129-180, (1992).

Baigre, S., "Electric Control Loading—A Low Cost, High Performance Alternative," Proceedings of the 12th Interservice/Industry Training Systems Conference, Orlando, Florida, Nov. 1990, pp. 247-254.

Ballard, J.W., et al., "Human-engineered Electromechanical Tactual Sensory Control System", Electrical Manufacturing, pp. 118-121, (Oct. 1954).

Bejczy, A., "Sensors, Controls, and Man-Machine Interface for Advanced Teleoperation," *Science*, vol. 208, No. 4450, pp. 1327-1335, 1980.

Brooks, F.P., et al., "Project Grope: Haptic displays for scientific visualization," Computer Graphics: Proc. of SIGGRAPH 90, vol. 24, pp. 177-185, (Aug. 1990).

Calder, B., "Design of a force-feedback touch-inducing actuator for teleoperator robot control," Thesis (B.S.)—Massachusetts Institute of Technology, Dept. of Mechanical Engineering, Cambridge, MA, (1983).

Ellis, R.E., et al., "Design and and Evaluation of a High-Performance Prototype Planar Haptic Interface", DSC-vol. 49, Advances in Robotics, Mechatronics and Haptic Interfaces, ASME 1993, pp. 55-64, (1993).

Gotow, J.K. et al, "Controlled Impedance Test Apparatus for Studying Human Interpretation of Kinesthetic Feedback," Proceedings of the 1989 American Control Conference, Pittsburgh, PA, Jun. 21-23, 1989, pp. 332-337, (1989).

Gotow, J.K., et al., "Perception of Mechanical Properties at the Man-Machine Interface," Proceedings of the 1987 IEEE International Conference on Systems, Man, and Cybernetics, Alexandria, VA, Oct. 20-23, 1987, pp. 688-689. (1987).

Hogan, N., et al, "Haptic illusions: Experiments on human manipulation and perception of "virtual objects","vol. 55 Cold Spring Harbor Symposia on Quantitative Biology, pp. 925-931, (1990).

IBM Corporation. "Mouse Ball-actuating Device with Force and Tactile Feedback," vol. 32 IBM Technical Disclosure Bulletin No. 9B, pp. 230-235 (Feb. 1990).

Iwata, H., "Artificial Reality with Force-feedback: Development of Desktop Virtual Space with Compact Master Manipulator," vol. 24 Computer Graphics No. 4. pp. 165-170, (1990).

Iwata, H., et al, "Volume Haptization", Proceedings of the IEEE 1993 Symposium on Research Frontiers in Virtual Reality, pp. 16-23, (1993).

* cited by examiner

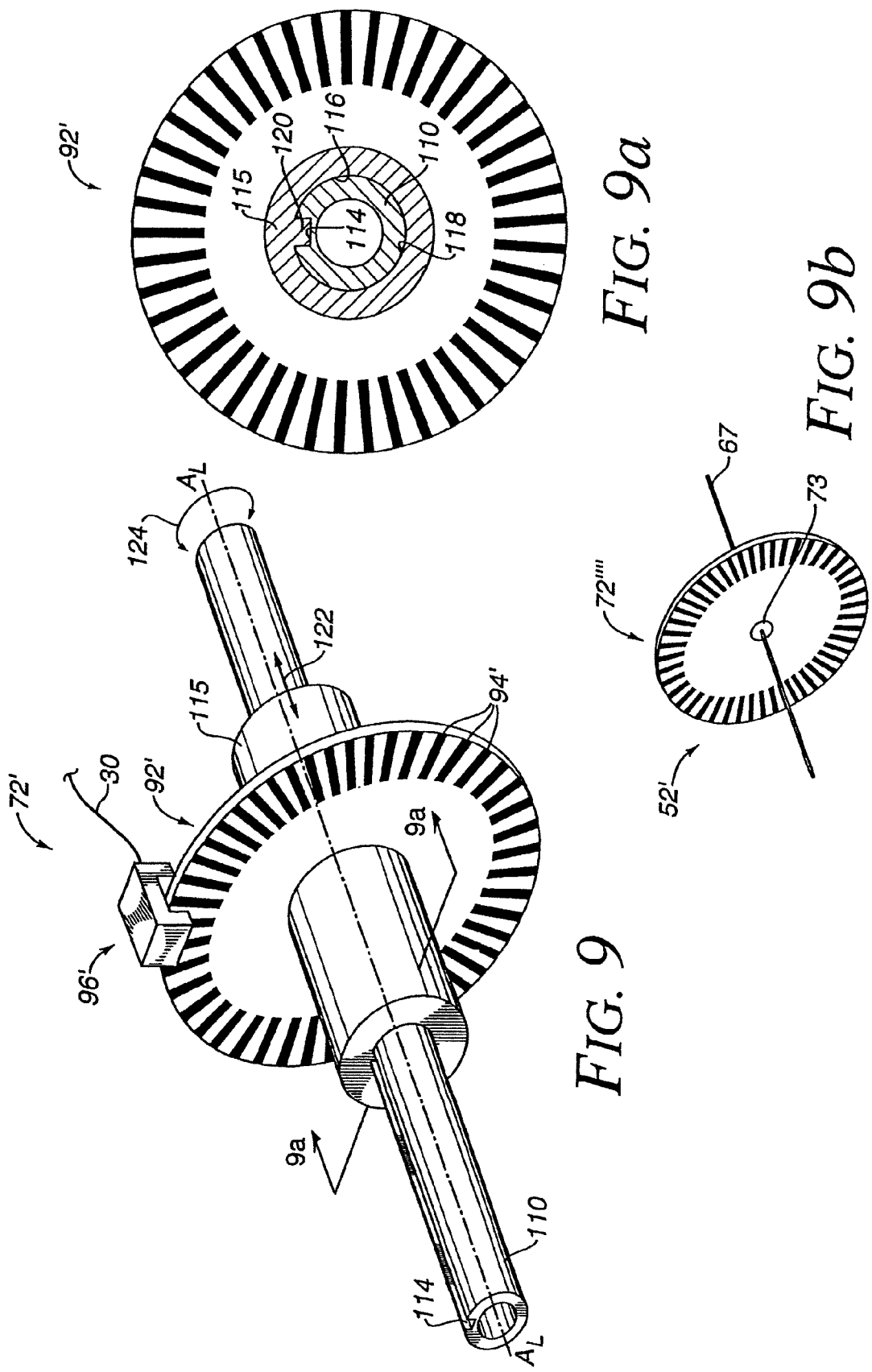

PHYSICALLY REALISTIC COMPUTER SIMULATION OF MEDICAL PROCEDURES

CROSS REFERENCE TO RELATED APPLICATIONS

This application is a continuation of U.S. application Ser. No. 11/725,958, filed Mar. 19, 2007, which is a continuation of U.S. application Ser. No. 10/674,423, filed Oct. 1, 2003, now U.S. Pat. No. 7,215,326, which is a continuation of U.S. application Ser. No. 09/996,487, filed Nov. 27, 2001, now U.S. Pat. No. 6,654,000, which is a continuation of U.S. application Ser. No. 09/276,012, filed Mar. 25, 1999, now U.S. Pat. No. 6,323,837, which is a continuation of application Ser. No. 08/833,502, filed Apr. 7, 1997 now U.S. Pat. No. 6,037,927, which is a continuation of application Ser. No. 08/275,120, filed Jul. 14, 1994, now Pat. No. 5,623,582, the entirety of all of which are hereby incorporated herein by reference.

BACKGROUND OF THE INVENTION

This invention relates generally to human/computer interface devices, and more particularly to computer input devices such as mice, trackballs, etc.

Virtual reality computer systems provide users with the illusion that they are part of a "virtual" environment. A virtual reality system will typically include a personal computer or workstation, specialized virtual reality software, and virtual reality I/O devices such as head mounted displays, pointer gloves, 3D pointers, etc.

For example, a virtual reality computer system can allow a doctor-trainee or other human operator or user to "manipulate" a scalpel or probe within a computer-simulated "body", and thereby perform medical procedures on a virtual patient. In this instance, the I/O device is typically a 3D pointer, stylus, or the like. As the "scalpel" or "probe" moves within the body image displayed on the screen of the computer system, results of such movement are updated and displayed so that the operator can gain the experience of such a procedure without practicing on an actual human being or a cadaver.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. Such procedures as laparoscopic surgery, catheter insertion, and epidural analgesia should be realistically simulated with suitable human/computer interface devices if the doctor is to be properly trained.

While the state of the art in virtual simulation and medical imaging provides a rich and realistic visual feedback, there is a great need for new human/computer interface tools which allow users to perform natural manual interactions with the computer simulation. For medical simulation, there is a strong need to provide doctors with a realistic mechanism for performing the manual activities associated with medical procedures while allowing a computer to accurately keep track of their actions.

There are number of devices that are commercially available for interfacing a human with a computer for virtual reality simulations. There are, for example, such 2-dimensional input devices such as mice, trackballs, and digitizing tablets. However, 2-dimensional input devices tend to be awkward and inadequate to the task of interfacing with 3-dimensional virtual reality simulations. In contrast, a 3-dimensional human/computer interface tool sold under the trademark Immersion PROBE™ is marketed by Immersion Human Interface Corporation of Palo Alto, Calif., and allows manual control in 3-dimensional virtual reality computer environments. A pen-like stylus allows for dexterous 3-dimensional manipulation, and the position and orientation of the stylus is communicated to a host computer. The Immersion PROBE has six degrees of freedom which convey spatial coordinates (x, y, z) and orientation (role, pitch, yaw) of the stylus to the host computer.

While the Immersion PROBE is an excellent 3-dimensional interface tool, it may be inappropriate for certain virtual reality simulation applications. For example, in some of the aforementioned medical simulations three or four degrees of freedom of a 3-dimensional human/computer interface tool is sufficient and, often, more desirable than five or six degrees of freedom because it more accurately mimics the real-life constraints of the actual medical procedure. Therefore, a less complex, more compact, lighter weight, lower inertia and less expensive alternative to six degree of freedom human/computer interface tool is desirable for certain applications.

SUMMARY

The present invention provides a 3-dimensional human/computer interface tool which is particularly well adapted to virtual reality simulation systems that require fewer degrees of freedom, e.g. two, three, or four degrees of freedom. The present invention therefore tends to be less complex, more compact, lighter weight, less expensive, more reliable and have less inertia than 3-dimensional human/computer interface tools of the prior art having more degrees of freedom.

The present invention is directed to a method and apparatus for providing an interface between a human and a computer. The human end of the interface is preferably a substantially cylindrical object such as a shaft of a surgeon's tool, a catheter, a wire, etc. Alternatively, it can comprise a pool cue, a screw driver shaft, or any other elongated object that is manipulated in 3-dimensional space by a human operator. In certain embodiments of the present invention, the computer develops signals to provide force feedback to the object. For example, a twisting or resisting force can be imparted on the object to provide haptic or force feedback of a medical procedure being performed in a virtual reality simulation.

An apparatus for interfacing with a electrical system includes a support, a gimbal mechanism coupled to the support, and preferably three electromechanical transducers, although certain embodiments (e.g. for use with catheters) may require only two electromechanical transducers. The gimbal mechanism has a base portion which is rotatably coupled to the support to provide a first degree of freedom, and an object receiving portion rotatably coupled to the base portion to provide a second degree of freedom. A first electromechanical transducer is coupled between the support and the base portion, a second electromechanical transducer is coupled between the base portion and the object receiving portion, and a third electromechanical transducer is coupled between the object receiving portion and an intermediate portion of an elongated object that is at least partially disposed within the object receiving portion. The third electromechanical transducer is associated with a third degree of freedom. Therefore, each of the three transducers are associated with a degree of freedom of movement of the object when it is engaged with the object receiving portion of the gimbal mechanism.

More specifically, an apparatus for interfacing an operator manipulable shaft with a computer includes a support, a gimbal mechanism, and four sensors. The gimbal mechanism preferably includes a U shaped base portion having a base and a pair of substantially parallel legs extending therefrom, where the base of the U shaped base portion is rotatably coupled to the support, and a shaft receiving portion pivotally coupled between the legs of the base portion. The shaft receiving portion includes a translation interface and a rotation interface that engage the shaft when it is engaged with an aperture of the shaft receiving portion. The base portion rotates around a first axis and the shaft receiving portion rotates around a second axis substantially perpendicular to the first axis, such that an axis of the shaft defines a radius in a spherical coordinate system having an origin at an intersection of the first axis and the second axis. A first sensor is coupled between the support and the U shaped base portion to provide a first output signal, a second sensor is coupled between the U shaped base portion and the shaft receiving portion to produce a second output signal, a third sensor is coupled to the translation interface to produce a third output signal, and a fourth sensor is coupled between the rotation interface and the object to produce a fourth output signal. The output signals are preferably coupled to an input of a computer by an electronic interface.

In an alternative embodiment of the present invention a first actuator is coupled between the support and the U shaped base portion to produce a movement therebetween in response to a first input electrical signal, a second actuator is coupled between the U shaped base portion and the shaft receiving portion to produce a movement therebetween in response to a second input electrical signal, a third actuator is coupled to the translation interface to produce a mechanical movement of the elongated cylindrical object relative to the shaft receiving portion in response to a third input electrical signal, and a fourth actuator is coupled to the rotation interface to produce a mechanical movement of the elongated cylindrical object relative to the shaft receiving portion in response to a fourth input electrical signal.

A method for providing a human/computer interface includes the steps of: (a) defining an origin in a 3-dimensional space; (b) physically constraining a shaft that can be grasped by an operator such that a portion of the object always intersects the origin and such that the portion of the object extending past the origin defines a radius in a spherical coordinate system; (c) transducing a first electrical signal related to a first angular coordinate of the radius in the spherical coordinate system with a first transducer; (d) transducing a second electrical signal related to a second angular coordinate of the radius in the spherical coordinate system with a second transducer; (e) transducing a third electrical signal related to the length of the radius with a third transducer; and (f) electrically coupling the transducers to a computer system to provide a human/computer interface. The method can further include the step of transducing a fourth electrical signal related to a rotation of the shaft around an axis with a fourth transducer. The transducers are either sensors, actuators, or bi-directional transducers which can serve as either input or sensors.

It will therefore be appreciated that a human/computer interface of the present invention includes a support, a gimbal mechanism coupled to the support, and an elongated shaft engaged with the gimbal mechanism and having a grip area that can be grasped by a hand of an operator. The gimbal mechanism has a base portion rotatably coupled to the support, and a shaft receiving portion rotatably coupled to the base. A first sensor is coupled between the support and the base portion, a second sensor is coupled between the base portion and the shaft receiving portion, and a third sensor is coupled between the shaft receiving portion and an intermediate portion of the shaft. The three sensors are coupled to an input of a computer to provide the human/computer interface. Preferably, the interface further includes a fourth sensor coupled between the shaft receiving portion and an intermediate portion of the shaft, where the third sensor is a translation sensor and the fourth sensor is a rotation sensor.

The advantage of the present invention is that a 3-dimensional human/computer interface tool is provided which has the three or four degrees of freedom available that are desirable for many virtual reality simulation applications. The mechanism of the present invention is relatively straightforward allowing for low cost production and high reliability. Furthermore, since the human/computer interface tool of the present invention is constrained from movement along at certain degrees of freedom, it can more accurately simulate the use of tools and other elongated mechanical objects which are similarly constrained. Importantly, the present interface is of low inertia since the primary mass of the interface is located at the pivot point. This, along with the light weight of the interface, makes the interface less fatiguing to use.

In another embodiment of the present invention a human/computer interface tool is provided which is provided with only two degrees of freedom. This is particularly advantageous when the shaft is flexible, such as with very thin shafts, wires, catheters, and the like. With, for example, catheters, it is only necessary to provide two degrees of freedom (i.e. in-and-out, and rotation) and, therefore, sensors and/or actuators for the other degrees of freedom do not need to be provided.

These and other advantages of the present invention will become apparent to those skilled in the art upon a reading of the following descriptions of the invention and a study of the several figures of the drawing.

BRIEF DESCRIPTION OF THE DRAWINGS

FIG. 2a is a perspective view of an alternative translation interface used for wires, catheters, and the like;

FIG. 9 is a perspective view of a sensor in accordance with the present invention;

FIG. 9a is a sectional view taken along line 9a-9a of FIG. 9.;

FIG. 9b is a perspective view of an alternative sensing wheel used for wires, catheters, and the like;

DETAILED DESCRIPTION

Figure 1:
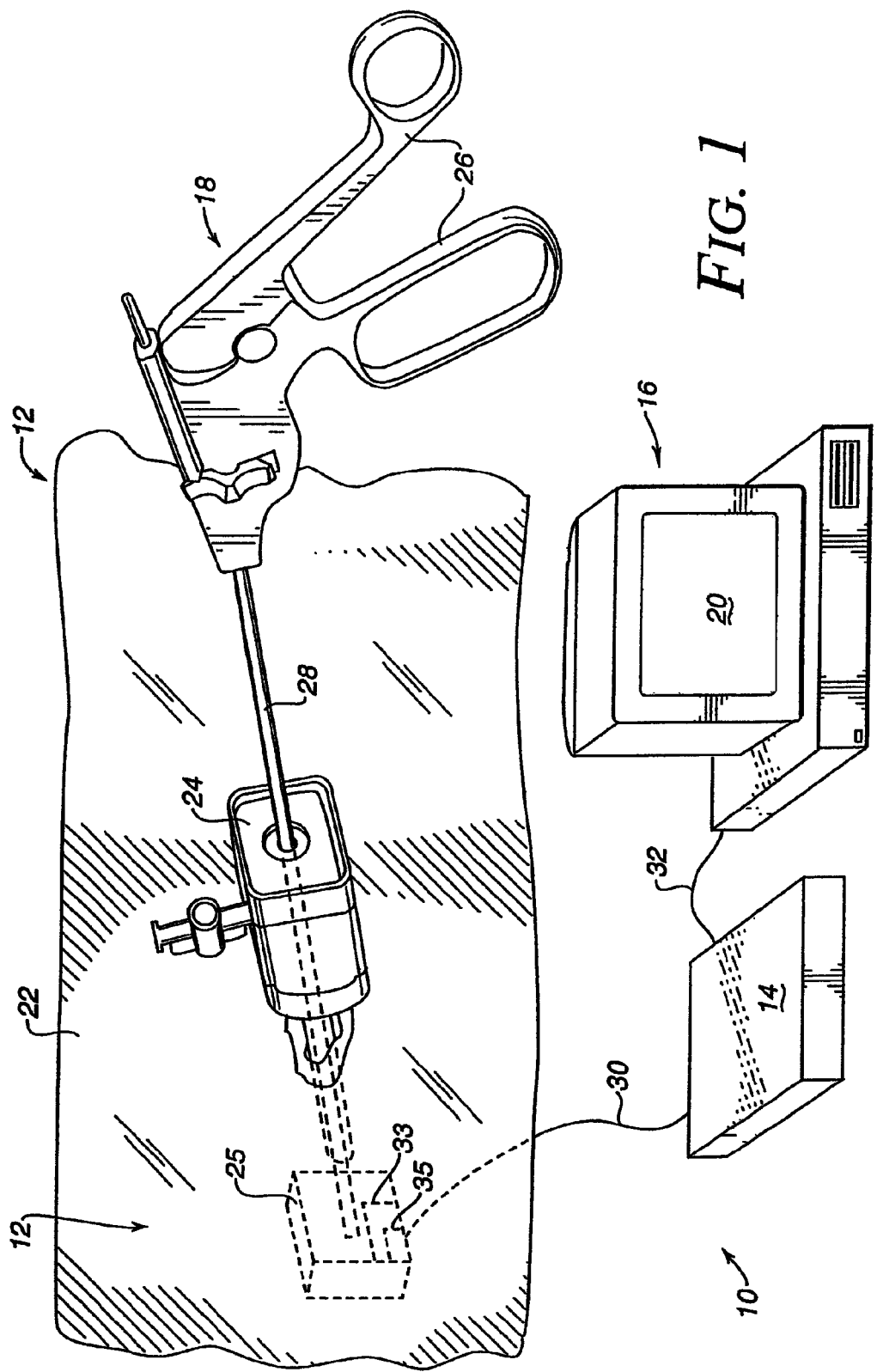
FIG. 1 is a perspective view of a virtual reality system which employs an apparatus of the present invention to interface a laparoscopic tool handle with a computer system.

In FIG. 1, a virtual reality system 10 includes a human/computer interface apparatus 12, a electronic interface 14, and a computer 16. The illustrated virtual reality system 10 is directed to a virtual reality simulation of a laparoscopic surgery procedure. The software of the simulation is not a part of this invention and thus will not be discussed in any detail. However, such software is commercially available as, for example, Teleos™ from High Techsplanations of Rockville, Md. Suitable software drivers which interface such simulation software with computer input/output (I/O) devices are available from Immersion Human Interface Corporation of Palo Alto, Calif.

A laparoscopic tool 18 used in conjunction with the present invention is manipulated by an operator and virtual reality images are displayed on a screen 20 of the digital processing system in response to such manipulations. Preferably, the digital processing system is a personal computer or workstation, such as an IBM-PC AT or Macintosh personal computer, or a SUN or Silicon Graphics workstation. Most commonly, the digital processing system is a personal computer which operates under the MS-DOS operating system in conformance with an IBM PC AT standard.

The human/interface apparatus 12 as illustrated herein is used to simulate a laparoscopic medical procedure. In addition to a standard laparoscopic tool 18, the human/interface apparatus 12 includes a barrier 22 and a standard laparoscopic trocar 24. The barrier 22 is used to represent portion of the skin covering the body of a patient. Trocar 24 is inserted into the body of the patient to provide an entry and removal point from the body of the patient for the laparoscopic tool 18, and to allow the manipulation of the laparoscopic tool 18 within the body of the patient while minimizing tissue damage. Laparoscopic tools 18 and trocars 24 are commercially available from sources such as U.S. Surgical of Connecticut. Preferably, the laparoscopic tool 18 is modified such that the end of the tool (such as any cutting edges) are removed, leaving only the handle and the shaft. The end of the laparoscopic tool 18 is not required for the virtual reality simulation, and is removed to prevent any potential damage to persons or property. A gimbal apparatus 25 is shown within the "body" of the patient in phantom lines.

The laparoscopic tool 18 includes a handle or "grip" portion 26 and a shaft portion 28. The shaft portion is an elongated mechanical object and, in particular, is an elongated cylindrical object. The present invention is concerned with tracking the movement of the shaft portion 28 in three-dimensional space, where the movement has been constrained such that the shaft portion 28 has only three or four free degrees of motion. This is a good simulation of the real use of a laparoscopic tool 18 in that once it is inserted into a trocar 24 and through the gimbal apparatus 25, it is limited to about four degrees of freedom. More particularly, the shaft 28 is constrained at some point of along its length such that it can move with four degrees of freedom within the patient's body.

While the present invention will be discussed with reference to the shaft portion 28 of laparoscopic tool 18, it will be appreciated that a great number of other types of objects can be used with the method and apparatus of the present invention. In fact, the present invention can be used with any elongated mechanical object where is desirable to provide a human/computer interface with three or four degrees of freedom. Such objects may include catheters, hypodermic needles, wires, fiber optic bundles, screw drivers, pool cues, etc. Furthermore, although the described preferred embodiment of the present invention contemplates the use of a elongated cylindrical mechanical object, other embodiments of the present invention provide a similar human/computer interface for an elongated mechanical objects which are not cylindrical in shape.

The electronic interface 14 is a part of the human/computer interface apparatus 12 and coupled the apparatus 12 to the computer 16. An electronic interface 14 that is particularly well adopted for the present is described in U.S. patent application Ser. No. 08/092,974, filed Jul. 16, 1993, now U.S. Pat. No. 5,576,727, assigned to the assignee of the present invention and incorporated herein by reference in its entirety. The electronic interface described therein was designed for the Immersion PROBE™ 3-D mechanical mouse and has six channels corresponding to the six degrees of freedom of the Immersion PROBE. However, in the context of the present invention, the electronic interface 14 requires the use of only four of the six channels, since the present invention is preferably constrained to no more than four degrees of freedom.

The electronic interface 14 is coupled to a gimbal apparatus 25 of the apparatus 12 by a cable 30 and is coupled to the computer 16 by a cable 32. In some embodiments of the present invention, interface 14 serves solely as an input device for the computer 16. In other embodiments of the present invention, interface 14 serves solely as an output device for the computer 16. In yet other embodiments of the present invention, the interface 14 serves as an input/output (I/O) device for the computer 16.

In an alternative embodiment of the present invention, interface 14 has a local microprocessor 33 preferably coupled with any transducers present in the interface 14 and with a transceiver 35. In such an embodiment, the computer 16 is coupled to the transceiver 35 and, typically, not coupled directly with any transducers present in the interface 14. As will be appreciated, the transceiver 35 may be any suitable transceiver capable of bidirectional communication through serial or parallel communication strategies. The local microprocessor 33 will be programmed to execute computer instructions locally such that a computing burden is removed from the computer 16. For example, positional information generated by the transducers may be processed locally by the local microprocessor 33, which in turn can send absolute position and velocity information to the computer 16. Still further, the local microprocessor 33 is capable of receiving incoming force commands from the computer 16, decoding such commands, and controlling the interface 14 accordingly. For more details, see U.S. Pat. No. 5,576,727 of Rosenberg et al."

Figure 2:
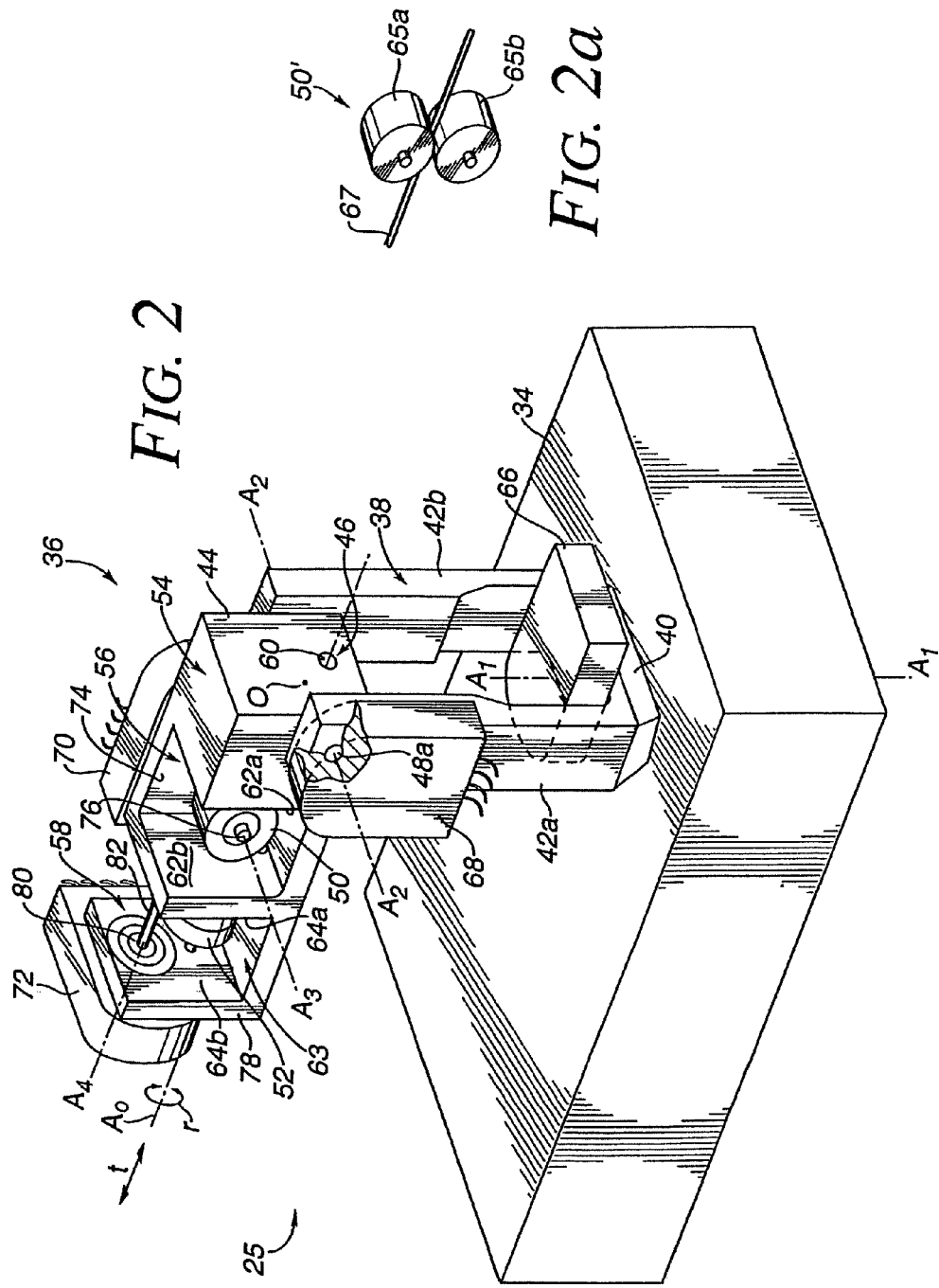
FIG. 2 is a perspective view of an apparatus for mechanically interfacing an elongated mechanical object with an electrical system in accordance with the present invention.

In the perspective view of FIG. 2, the gimbal apparatus 25 of the present invention is illustrated in some detail. The gimbal apparatus 25 includes a support 34 and a gimbal mechanism 36 rotatably coupled to the support. The gimbal mechanism 36 preferably includes a U shaped base portion 38 including a base 40 and a pair of substantially parallel legs 42a and 42b extending upwardly therefrom. As used herein, "substantially parallel" will mean that two objects or axis are exactly or almost parallel, i.e. are at least within five or ten degrees of parallel, and are preferably within less than one degree of parallel. Similarly, the term "substantially perpendicular" will mean that two objects or axis are exactly or almost perpendicular, i.e. at least within five degrees or ten degrees of perpendicular, or more preferably within less than one degree of perpendicular.

The gimbal mechanism 36 also includes an elongated object (shaft) receiving portion 44 provided with an aperture 46 which extends entirely through the object receiving portion. The aperture 46 defines an object axis $A_0$ for an elongated cylindrical object, such that the shaft portion 28 of the laparoscopic tool 18 of FIG. 1. The object receiving portion 44 is at least partially disposed between the legs 42a and 42b of the U shaped base portion, and is pivotally coupled thereto such as by a pair of pivots, one of which is shown as pivot 48a in leg 42a. Another pivot 48b (not shown) is provided in leg 42b.

The object receiving portion 44 also includes a translation interface 50 and a rotation interface 52. The object receiving portion 44 includes a bearing section 54, a translation sensor section 56, and a rotation sensor section 58. The bearing section 54 includes a mass of material provided with a cylindrical bore 60 forming a portion of the aperture 46. The translation sensor section 56 includes a pair of opposing wall surfaces 62a and 62b, each of which is provided with a cylindrical bore receptive to the cylindrical object and forming a part of the aperture 46 which extends through the object receiving portion. The translation sensor section 56 includes a pair of opposing wall surfaces 64a and 64b of a wall 63 and which are provided with cylindrical bores receptive to the cylindrical object and therefore also forming a part of the aperture 46. In consequence, when an elongated cylindrical object is inserted into the object receiving portion 44 along axis $A_0$ it engages the bore 60 of the bearing section 54, and extends through bores provided in the surfaces 62a, 62b, 64a, and 64b to extend completely through the object receiving portion 44 along aperture 46. In another embodiment of the present invention, wall 63 (and therefore wall surfaces 64a and 64b) is eliminated as being superfluous.

Referring briefly to FIG. 2a, an alternative construction for the translation interface 50 of FIG. 2 is shown at 50'. This alternative translation interface 50' is well adapted for very thin shafts, wires, catheters, and the like. The problem encountered with the translation interface 50 is that, for example, wires and catheters are flexible and therefore do not engage well with a single friction wheel. Therefore, the translation interface 50' includes a drive wheel 65a that is coupled to a sensor and/or actuator, and an idler wheel 65b. The wire or catheter 67 is pinched between the drive wheel 65a and the idler wheel 65b so that there is good frictional engagement between the catheter 67 and the drive wheel 65a.

The object receiving portion 44 is preferably a unitary mass of material made from aluminum or some other lightweight material such as a plastic. The object receiving portion 44 is preferably cast, molded, and/or machined as a monoblock member having the aforementioned bearing section, translation sensory section, and rotation sensory section. The materials and construction of U shaped base portion 38 preferably match the materials and construction techniques used for the production of object receiving portion 44.

The gimbal apparatus 25 illustrated in FIG. 2 constrains an object that is engaged with the object receiving portion 44 to four degrees of freedom. This is accomplished by allowing the U shaped base portion 38 to rotate around an axis $A_1$ relative to the support 34, by allowing the object receiving portion 44 to rotate around an axis $A_2$ relative to the U shaped base portion 38, by allowing the object to translate as illustrated by the arrow t along axis $A_0$ of aperture 46, and by allowing the object to rotate as indicated by arrow r around the axis $A_0$ of aperture 46.

Four electromechanical transducers are used in association with these four degrees of freedom. More particularly, a first degree of freedom electromechanical transducer 66 is arranged to transduce motion and/or force between the U shaped base portion 38 and the support 34, a second degree of freedom electromechanical transducer 68 is arranged to transduce motion and/or force between the U shaped base portion 38 and the object receiving portion 44, a third degree of freedom electromechanical transducer 70 is arranged to transduce motion and/or force between the object receiving portion 44 and an object engaged with the object receiving portion 44, and a fourth degree of freedom transducer 72 is arranged to transduce motion and/or force between the object receiving portion 44 and an object engaged with the object receiving portion 44.

By "associated with", "related to", or the like, it is meant that the electromechanical transducer is influenced by or influences one of the four degrees of freedom. The electromechanical transducers can be input transducers, in which case they sense motion along a respective degree of freedom and produce an electrical signal corresponding thereto for input into computer 16. Alternatively, the electromechanical transducers can be output transducers which receive electrical signals from computer 16 that cause the transducers to impart a force on the object in accordance with their respective degrees of freedom. The electromechanical transducers can also be hybrid or bi-directional transducers which operate both as sensors and as actuator devices.

A variety of transducers, readily available in the commercial market are suitable for use in the present invention. For example, if the transducers are input transducers ("sensors"), such sensors can include encoded wheel transducers, potentiometers, etc. Output transducers ("actuators") include stepper motors, servo motors, magnetic particle brakes, friction brakes, pneumatic actuators, etc. Hybrid or bidirectional transducers often pair input and output transducers together, but may also include a purely bi-directional transducer such as a permanent magnet electric motor/generator.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the shaft is placed in a known position within the gimbal mechanism and a calibration signal is provided to the system to provide the reference position mentioned above. All angles provided by the sensors are thereafter relative to that reference position. Such calibration methods are well known to those skilled in the art and, therefore, will not be discussed in any great detail herein.

A preferred input transducer for use of the present invention is an optical encoder model SI marketed by U.S. Digital of Vancouver, Wash. This transducer is an encoded wheel type input transducer. A preferred output transducer for use of the present invention is a d.c. motor model 2434.970-50 produced by Maxon of Fall River, Mass. This type of transducer is a servo motor type output transducer.

There are a number of ways of attaching the transducers to the various members of the gimbal apparatus 25. In this preferred embodiment, a housing of transducer 66 is attached to the U shaped base portion 38, and a shaft of the transducer extends through an oversize bore (not shown) in base 40 to engage a press-fit bore (also not shown) in support 34. Therefore, rotation of the us shaped base portion 38 around axis $A_1$ will cause a rotation of a shaft of transducer 66. A housing of transducer 68 is attached to leg 42a of the U shaped base portion 38 such that its shaft forms pivot 48a. Therefore rotation of the object receiving portion 44 around axis $A_2$ will cause a rotation of the shaft of a second transducer 68. The transducer 70 is attached to object receiving portion 44 and extends through a bore (not shown) in a wall 74 of the translation sensor section 56. The shaft 76 provides an axis about which the translation interface 50 can rotate. The fourth transducer 74 is attached to a wall 78 of rotation sensor section 58 and extends through a bore 80 in that wall 78. The shaft 82 of the transducer 72 engages a circumferential surface of rotation interface 52 and rotates therewith.

Axes $A_1$ and $A_2$ are substantially mutually perpendicular and intersect at an origin point O within object receiving portion 44. Axis $A_0$ also intersects this origin O. Shaft 76 rotates around an axis $A_3$ which is substantially perpendicular to the axis $A_0$. Shaft 58 of transducer 72 rotates around an axis $A_4$ which is substantially parallel to the axis $A_0$.

Figure 3:
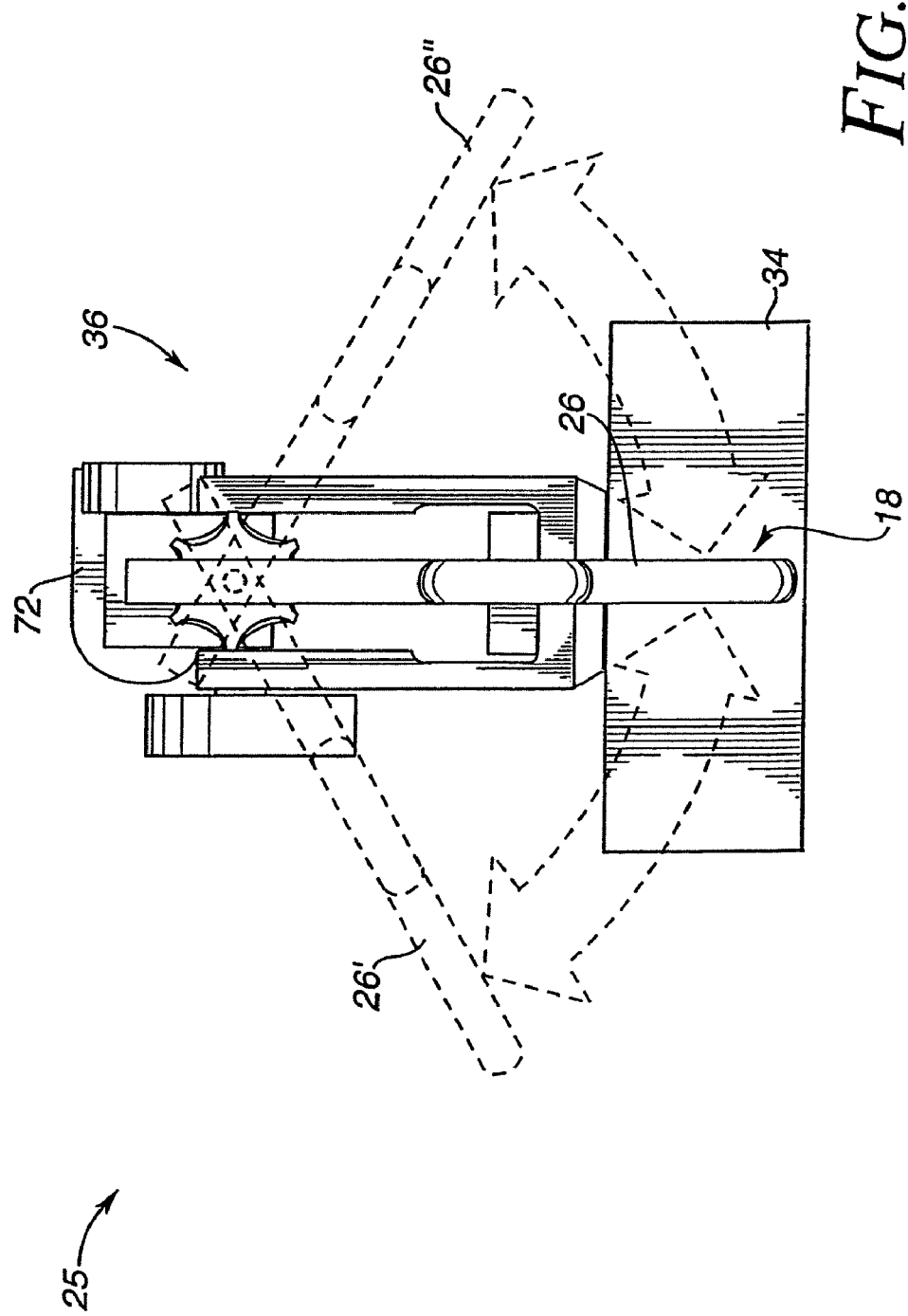
FIG. 3 is front elevation view of the apparatus of FIG. 2 illustrating a laparoscopic tool engaged with an object receiving portion of the present invention.

In FIG. 3, a front view of the gimbal apparatus 25 is used to illustrate one of the degrees of motion of the laparoscopic tool 18. The illustrated degree of freedom is the fourth degree of freedom, i.e. rotation around axis $A_0$ as illustrated by the arrow r in FIG. 2. This degree of freedom is detected by transducer 72. In this fourth degree of motion, the handle portion 26 of the laparoscopic tool 18 can rotate in a clockwise direction as indicated at 26' and in a counter clockwise direction as indicated at 26". Of course, the handle 26 can rotate a full 360° although this would require the release and re-grasping of the handle 26.

Figure 4:
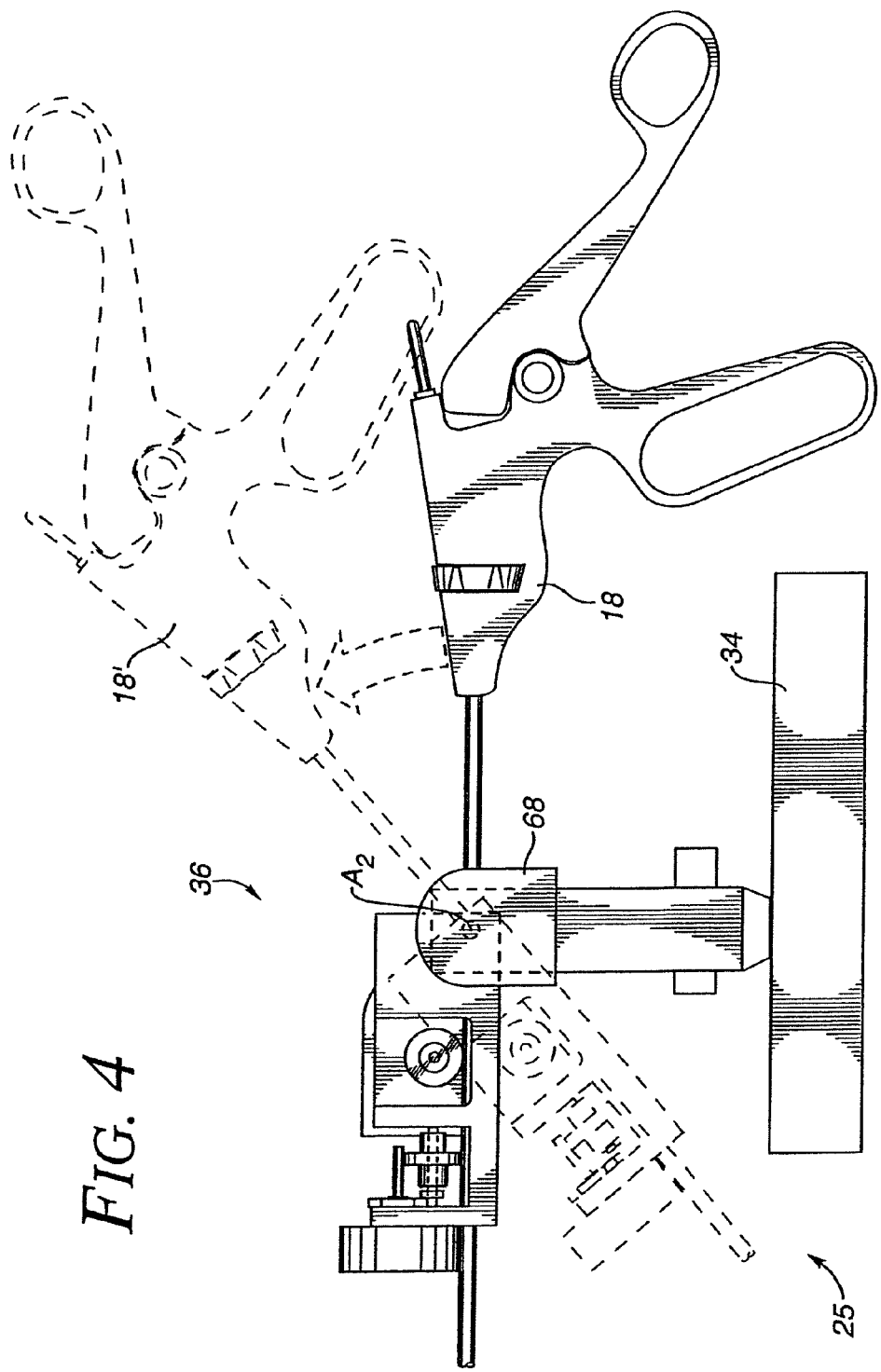
FIG. 4 is a side elevation similarly showing a laparoscopic tool engaged with the object receiving portion of the present invention.

In FIG. 4, a second degree of freedom is illustrated. With this degree of freedom, the laparoscopic tool 18 can pivot upwardly as illustrated at 18' or downwardly (not shown). This rotation around $A_2$ is detected by transducer 68. It should be noted in the present embodiment, the laparoscopic tool 18 cannot rotate 360° around the axis $A_2$ because it is physically constrained by the support 34, portions of the gimbal mechanism 36, etc. However, in the present embodiment, the laparoscopic tool can achieve approximately 170 degrees of rotation around axis $A_2$.

Figure 5:
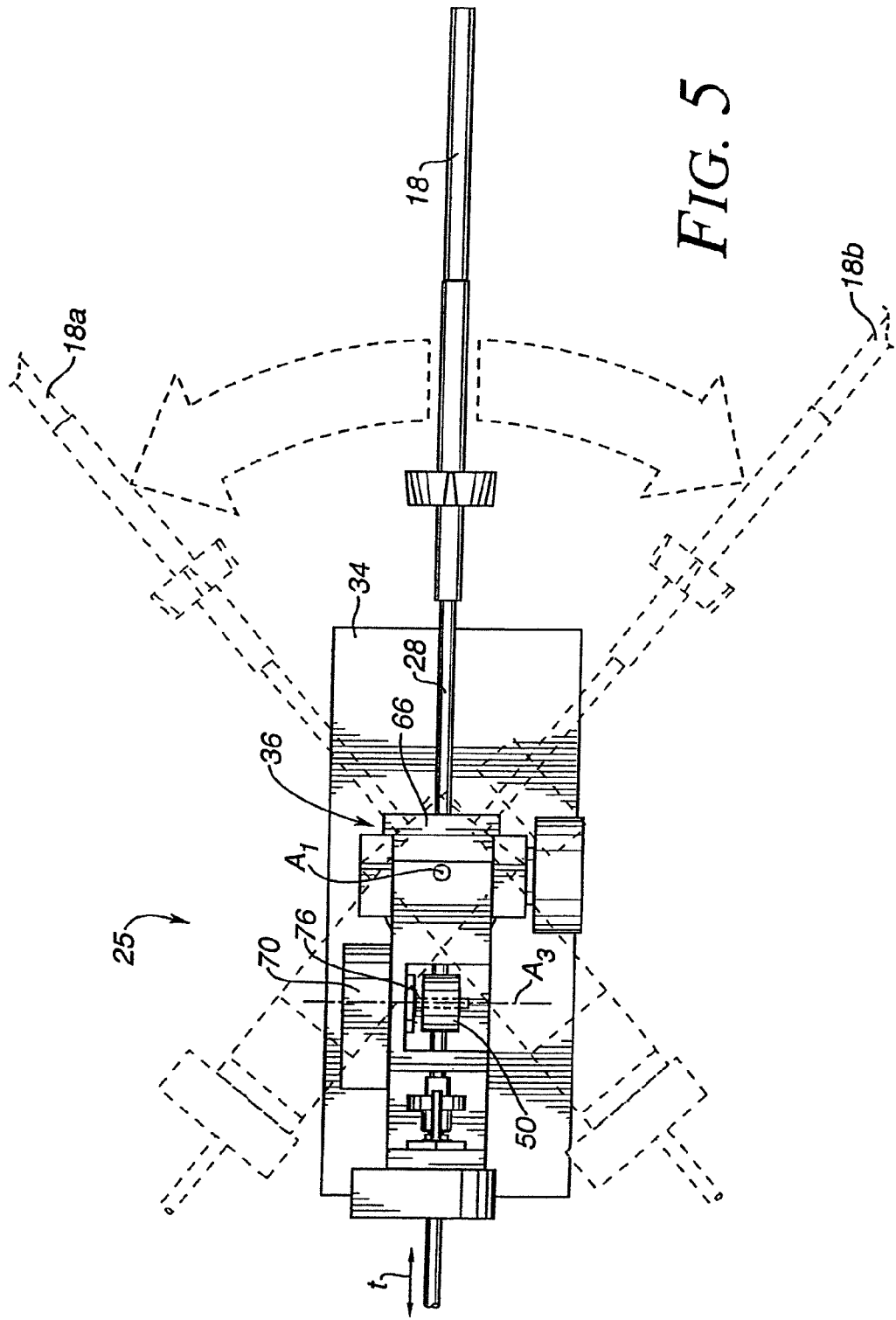
FIG. 5 is a top plan view also illustrating the engagement of a laparoscopic tool with the object receiving portion of the present invention.

FIG. 5 is top view of the gimbal apparatus 25 and illustrates the first and third degrees of freedom. The first degree of freedom is detected by transducer 66 as the laparoscopic tool 18 is pivoted or rotated around axis $A_1$ as illustrated at 18a and 18b. The third degree of freedom is detected by transducer 70 as the shaft portion 28 of laparoscopic tool 18 is moved back and fourth as illustrated by the arrow "t." This causes a rotation of translation interface 50 and the shaft 76 of the third transducer 70.

Figure 6:
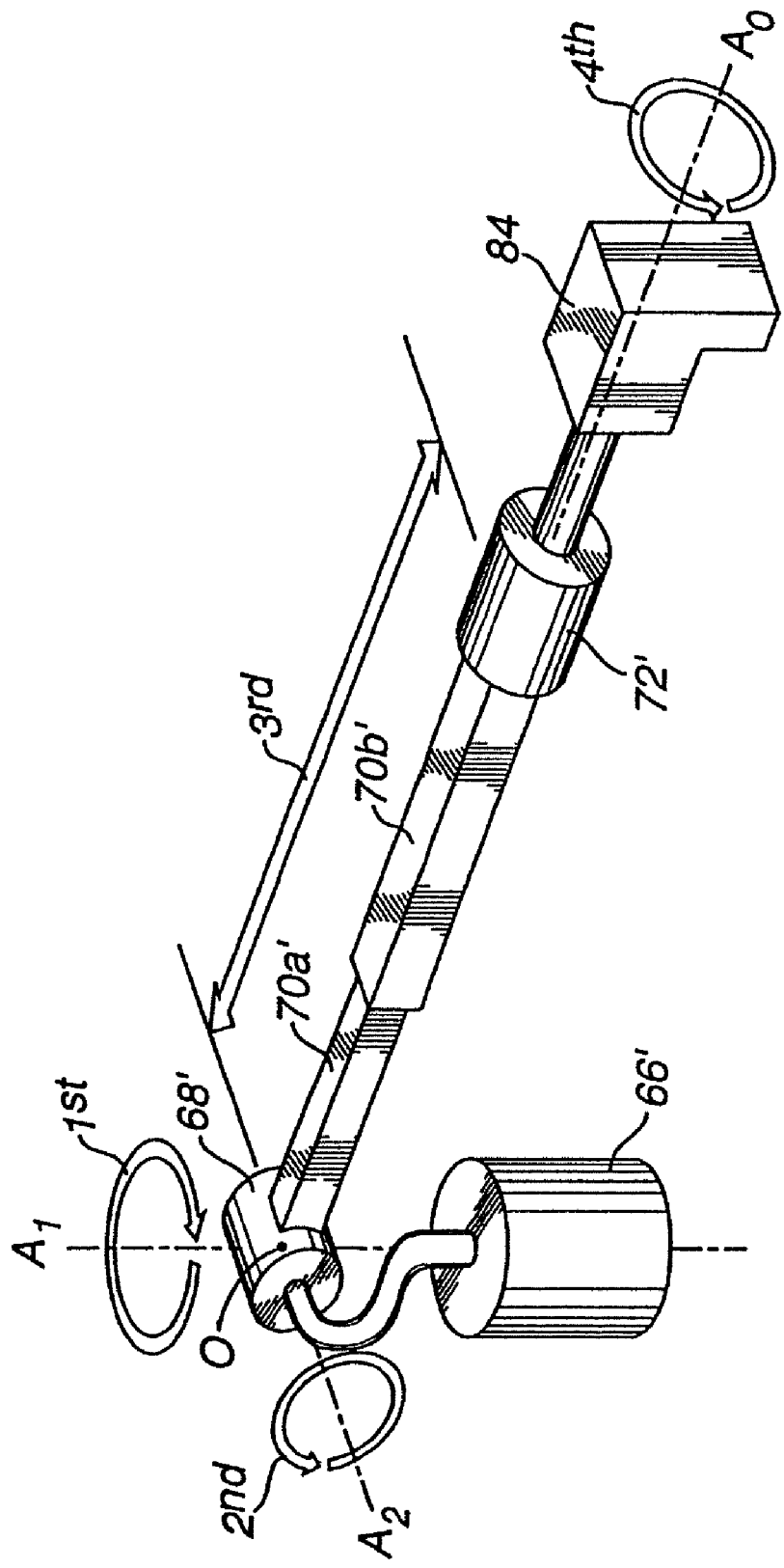
FIG. 6 is a pictorial view illustrating the four degrees of freedom enjoyed with the mechanism of the present invention.

The four degrees of freedom are illustrated graphically in FIG. 6. The cylinder 66' represents the first transducer 66 and allows a first degree of freedom labeled "1st" around axis $A_1$. Cylinder 68' represents the sensor 68 and allows a second degree of freedom labeled "2nd" around axis $A_2$. Telescoping members 70a' and 70b' represent the third sensor 70 can sense movement along a third degree of freedom labeled "3rd" along axis $A_0$. Finally, a cylinder 72' attached to member 70b' represents the fourth transducer 72 and senses a fourth degree of freedom labeled "4th" around axis $A_0$. A member 84 is provided to indicate position and rotational direction relative to axis $A_0$.

Figure 7:
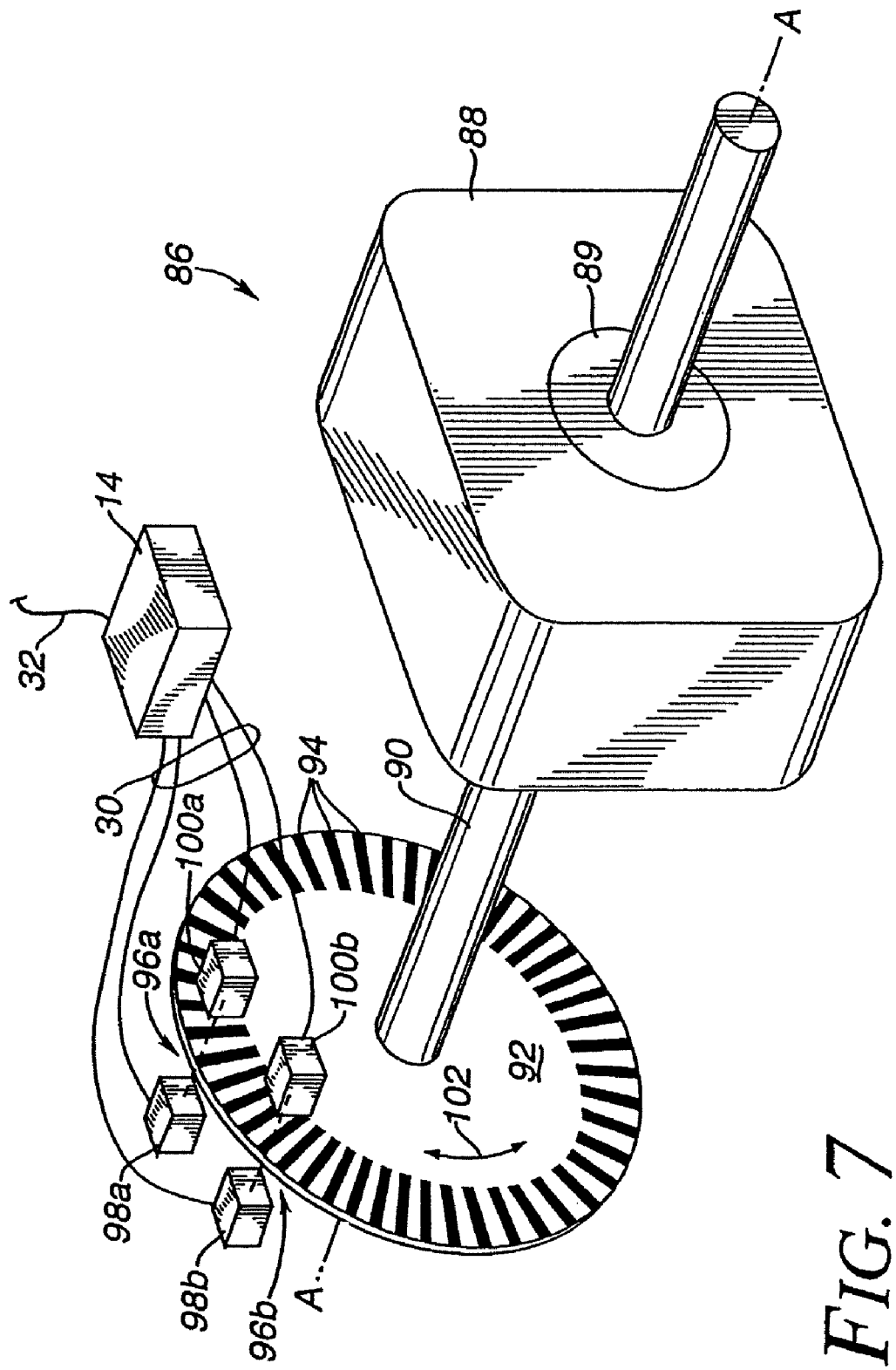
FIG. 7 illustrates a first embodiment of an input sensor.

In FIG. 7, a preferred input transducer (sensor) of the present invention is disclosed. Again, an input transducer of this type can be purchased as sensor model SI from U.S. Digital of Vancouver, Wash. The input transducer 86 includes a bearing block 88 having a bearing 89, a rotary shaft 90 supported by the bearing 89, and a sensing wheel 92 supported for rotation by shaft 90. The sensing wheel is preferably made from a clear, plastic material and is provided with a number of dark radial bands 94 near its circumference, such as by printing or silk screening. A first photodetector pair 96a including a light source 98a and a detector 100a are positioned on opposing sides of the sensing wheel 92 in alignment with the bands 94. Similarly, a second photodetector pair 96b including a light source 98b and a detector 100b are positioned on opposing sides of the sensing wheel 92 in alignment with the bands 94. As the sensing wheel 92 rotates as illustrated at 102 around an axis A, the bands 94 alternatively allow light emanating from light sources 98a and 98b to impinge or not impinge upon the detectors 100a and 100b, respectively. The electronic interface 14, coupled to the photodetector pairs 96a and 96b by cable 30, counts the bands 94 as they pass the photodetector pairs 96a and 96b to provide a signal on cable 32 to the computer 16 indicating the rotational position of the shaft 90 around axis A. The two pairs 96a and 96b are provided to determine the direction of rotation, as is well known to those skilled in the art of sensor design.

Figure 8:
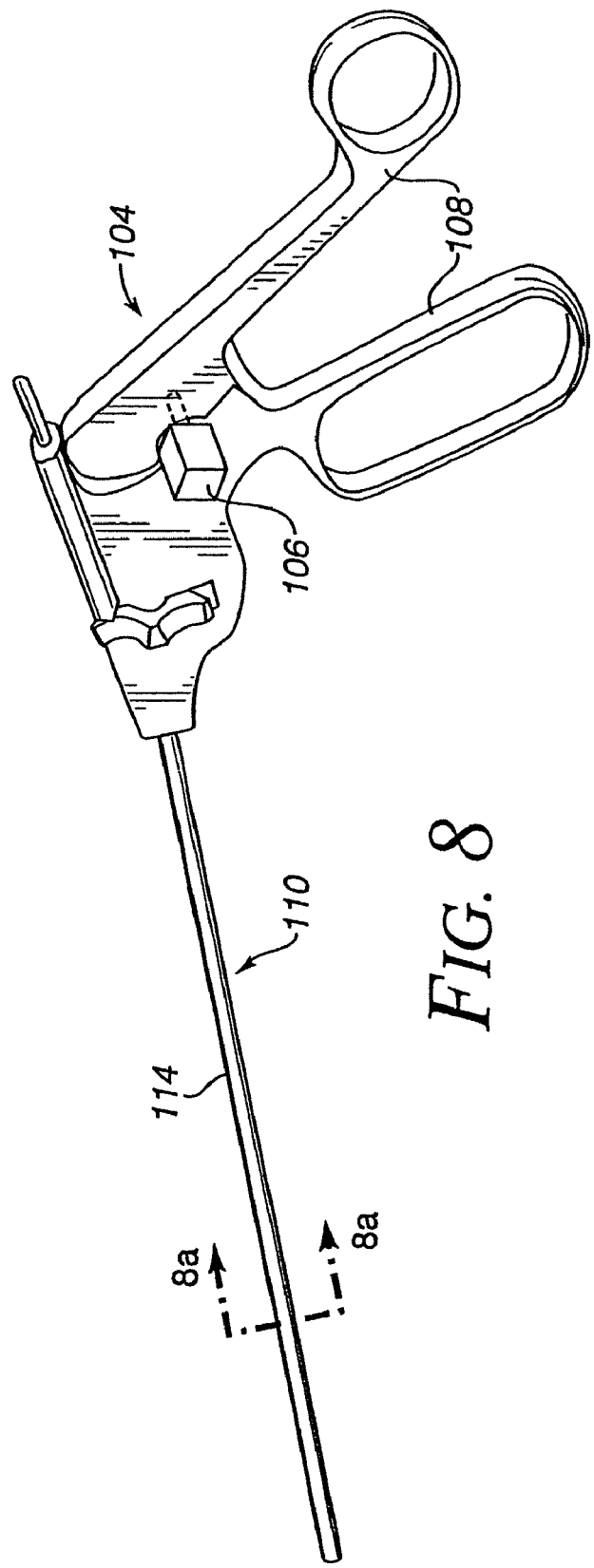
FIG. 8 illustrates a modified laparoscopic tool handle for the use of the present invention.
Figure 8A:
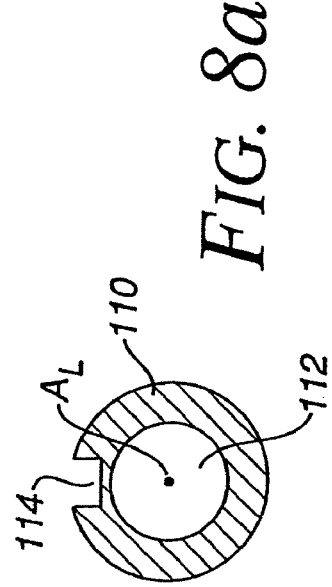
FIG. 8a is a cross-section taken along line 8a-8a of FIG. 8.

FIGS. 8 and 8a illustrate a modified laparoscopic tool 104. More particularly, a sensor 106 has been added to determine when the handle 108 has been squeezed, and the shaft 110 has been grooved or slotted for a purpose to be discussed subsequently. The sensor 106 can be coupled to the computer 16 through electronic interface 14 to provide additional input to the virtual reality system.

With reference to FIG. 8a, the shaft 110 is preferably hollow, having an axial bore 112 which aligns with axis $A_0$, and is provided with an elongated groove 114 which is parallel to an axis $A_L$ of the shaft 110. This elongated groove 114 can be produced by any process including extruding the shaft 110 in the appropriate shape, or cutting the groove 114 with a machine tool, etc.

FIGS. 9 and 9a illustrate an alternate embodiment for transducer 72 which utilizes the shaft 110 and a detector mechanism similar to the one illustrated in FIG. 7. More particularly, the transducer 72' includes a sleeve 114 which is slidingly engaged with shaft 110. As seen in the cross sectional view of FIG. 9a, the sleeve 115 is a substantially cylindrical object having a central bore 116 which engages the circumference 118 of the shaft 110. The sleeve 115 has a key 120 which engages the groove 114 of the shaft 110. Therefore, while the sleeve can slide back and forth along the axis $A_L$ as indicated at 122, but the sleeve 115 rotates with the shaft 110 as indicated at 124 due to the engagement of the key 120 with the groove 114. A sensing wheel 92' is affixed to a circumferential portion of sleeve 115 so that it rotates coaxially with the sleeve 115. A photodetector pair 96' senses the motion of bands 94' and produces an electrical signal on cable 30. The advantage of the embodiment shown in FIG. 9 and 9a is that rotation of the shaft around axis $A_L$ is detected without the possibility of slippage. Another advantage of this embodiment is that it is more compact in design.

In FIG. 9b an alternate embodiment for a rotation interface 52' is shown. This alternate embodiment is well adapted for flexible shafts, wires, catheters and the like, such as the aforementioned catheter 67. The rotation interface 52' includes a transducer 72"" that is provided with a resilient grommet 73 having a hole that engages a circumferential portion of the catheter 67. The grommet 73 is preferably a rubber or plastic grommet that causes the catheter 67 to rotate coaxially as the catheter spins or rotates. Preferably, the mass of the transducer 72"" is kept very small so that it only takes a small amount of friction to ensure coaxial rotation of the catheter and transducer without slippage. Because the level of friction is so small, it does not substantially impede translational motion (i.e. in-out motion) of the catheter.

Figure 10A:
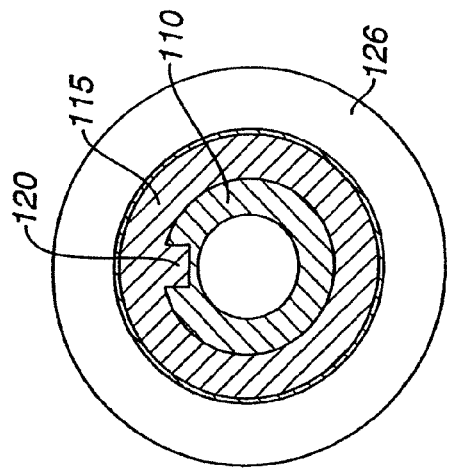
FIG. 10a is a cross sectional view taken along line 10a-10a of FIG. 10.
Figure 10:
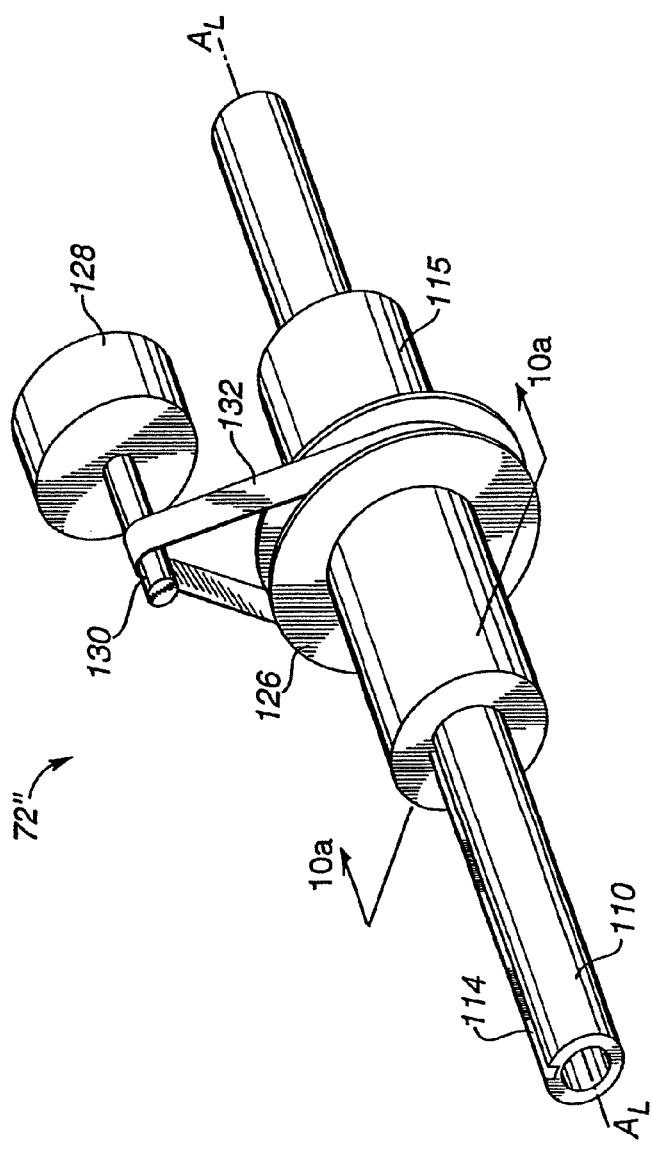
FIG. 10 is a perspective view of and alternative sensor mechanism of the present invention.

FIGS. 10 and 10a illustrate another embodiment 72" for the transducer 72 of FIG. 2 This embodiment has a number of points of similarity with the embodiment discussed with reference to FIGS. 9 and 9a, and it will be appreciated that elements with like reference numerals operate in a similar fashion. However, the embodiment of FIGS. 10 and 10a include a sheave 126 affixed to the circumference of sleeve 115 in the place of the sensing wheel 92' of FIG. 9 and FIG. 9a. A position sensor 128 has a shaft 130 which is coupled to the sheave 126 by a belt 132. The belt 132 can be any continuous loop structure including a resilient, rubber-type belt, a drive-chain type belt, etc. The shaft 130 of position sensor 128 therefore rotates with the sheave 126. The advantage of using a belt 132 or the like is that a substantial amount of force may be applied to the belt to, again, minimize slippage.

Figure 11A:
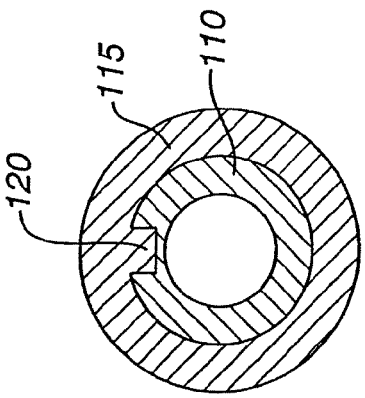
FIG. 11a is a sectional view taken along line 11a-11a of FIG. 11.
Figure 11:
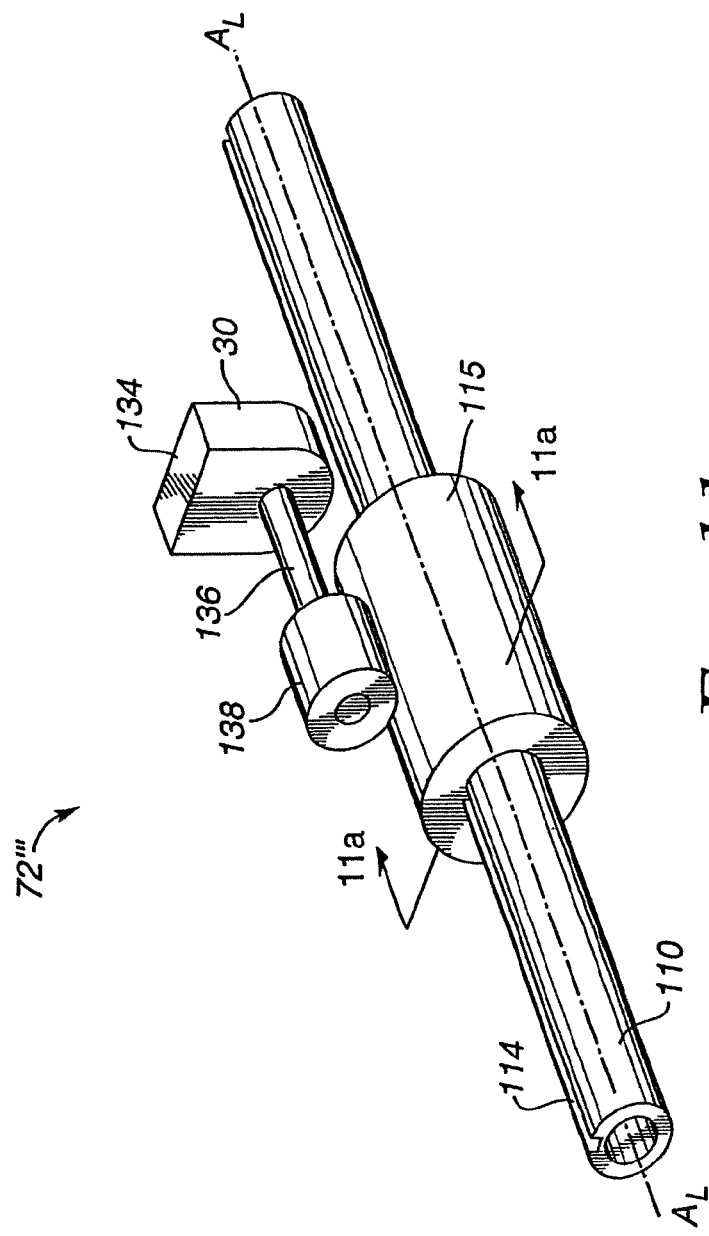
FIG. 11 is a perspective view of another alternative sensor of the present invention.

Another embodiment 72''' for the fourth transducer is illustrated in FIGS. 11 and 11a. Again, there are a number of points of similarity between the embodiments of FIGS. 11 and 11a and the previously described embodiments of FIGS. 9 and 9a and FIGS. 10 and 10a. Therefore like reference numerals will again refer to like elements. In this embodiment, a sensor 134 haws a shaft 136 which serves as the axle of a friction wheel 138 which, in turn, engages a circumferential surface of sleeve 115. Therefore, a rotation of the shaft 110 will cause a rotation of the sleeve 115, which will cause a rotation of the wheel 138 and the shaft 136 to create an electrical signal on cable 30.

With reference to all of the figures, and with particular reference to FIGS. 1 and 2, the shaft 28 of a laparoscopic tool 18 is inserted into aperture 46 along axis $A_0$, causing the shaft 28 to frictionally engage the translation interface (wheel) 50. In this instance, the translational interface 50 is a friction wheel made out of a rubber-like material. The shaft 28 is also in engagement with the rotational interface 52 which, in the embodiment of FIG. 2, is also a frictional wheel made out of a rubber-like material. Rotation of the shaft 28 around the axis $A_0$ is illustrated by the arrow r will cause a rotation of the friction wheel 50 and therefore the shaft 82 of the sensor 72. A translation of the shaft 28 along with axis $A_0$ will cause a rotation of the friction wheel 50 which rotates the shaft 76 of the transducer 70. A movement up or down of the laparoscopic tool 18 will cause a rotation of the shaft (pivot) 48a of transducer 68, and a side-to-side pivoting of the laparoscopic tool 18 will cause a rotational around axis $A_1$ which is detected by transducer 66.

To this point, the majority of the discussion has been under the assumption that the transducers are input transducers, i.e. the human/computer interface device is used an input device to the computer 16. However, it is also been mentioned that the interface device 12 can serve as an output device for the computer 16. When used as an output device, output transducers ("actuators") are used to respond to electrical signals developed by the computer 16 to impart a force upon the shaft 28 of the laparoscopic tool 18. This can provide useful movement and force (haptic) feedback to the doctor/trainee or other user. For example, if the laparoscopic tool encounters dense mass of tissue or a bone in the "virtual" patient, a force can be generated by transducer 70 making it harder for the doctor/trainee to push the shaft 28 further into the gimbal apparatus 25. Likewise, twisting motions can be imparted on the shaft 28 when the shaft encounters an obstacle within the virtual patient.

It should be noted that force applied to the shaft may not result in any movement of the shaft. This is because the shaft may be inhibited from movement by the hand of the operator who is grasping a handle or grip portion of the shaft. However, the force applied to the shaft may be sensed by the operator as haptic feedback.

With reference to FIG. 2, a method for mechanically interfacing an elongated mechanical object with an electrical system in accordance with the present invention includes first step of defining an origin in 3-dimensional space. This corresponds to the origin O at the intersection of axis $A_1$ and $A_2$. A second step is to physically constrain an elongated object in the 3-dimensional space such that a portion of the object always intersects the origin O and such that a portion of the object extending from the origin O defines a radius in a spherical coordinate system. The elongated object (such as shaft 28 of laparoscopic tool 18) is physically constrained in a 3-dimensional space by the aperture 46 of the object receiving portion 44. The portion of the shaft 28 extending from origin O defines the radius. A third step includes transducing a first electrical signal related to a first angular coordinate of the radius with a first transducer. This corresponds to the operation of transducer 66 which transduces a first electrical signal related to a first angular coordinate of the radius. A fourth step is transducing a second electrical signal related to a second angular coordinate of the radius. This corresponds to the operation of transducer 68 which transduces a second electrical signal. A fifth step is to transduce a third electrical signal related to the length of the radius, which corresponds to the operation of transducer 70. A sixth and final step is to electrically couple the transducers to an electrical system which, in this instance, is preferably a computer 16. An additional, optional step transduces a fourth electrical signal related to a rotation of the object around an object axis which intersects the origin O. This step corresponds to the operation of transducer 72. The transducers can be input transducers, output transducers, or bidirectional transducers.

It will be noted that the electrical system most frequently described in the present invention is a digital processing system or a computer. However, other digital systems, analog systems, and simple electric or electromechanical system can also be utilized with the apparatus and method of the present invention.

It will also be noted that while specific examples of "elongated objects" and "shafts" have been given, that these examples are not meant to be limiting. In general, equivalents of "elongated objects", "elongated cylindrical objects", "shafts", etc. include any object which can be grasped by a human operator to provide an interface between the operator and a computer system. By "grasp", it is meant that operators may releasably engage a grip portion of the object in some fashion, such as by hand, with their fingertips, or even orally in the case of handicapped persons. The "grip" can be a functional grip or handle attached to an elongated portion of the object, or can be a portion of the object itself, such as a portion of the length of a shaft that can be gripped and/or manipulated by the operator.

It should also be noted that flexible shafts, such as wires or catheters, do not always require three or four degrees of freedom. For example, if a human/computer interface for a catheter insertion virtual reality system is desired, only a translation interface (e.g. translation interface 50' of FIG. 2a)

and rotation interface (such as rotation interface 52' of FIG. 9c) may be required. This is because a catheter can be moved in and out of a virtual patient (as sensed by translation interface 50') and can be twisted or rotated (as sensed by rotation interface 50'), but cannot be, in any practical manner, moved up or down or from side-to-side due to the flexibility of the catheter. In such applications, therefore, it is desirable to have a human/computer interface with only two degrees of freedom.

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims include all such alternatives, modifications, permutations and equivalents as fall within the true spirit and scope of the present invention.

What is claimed is:

1. A system comprising:
   a user manipulatable object comprising a laparoscopic tool handle and an elongated member extending from the laparoscopic tool handle;
   a gimbal mechanism coupled to the user manipulatable object, the gimbal mechanism configured to receive the elongated member of the user manipulatable object and to allow the user manipulatable object to move in at least three rotational degrees of freedom and a translational degree of freedom;
   a trocar coupled to the gimbal mechanism, the trocar configured to receive the elongated member of the user manipulatable object;
   a first sensor configured to determine a first movement of the user manipulatable object in a first rotational degree of freedom and to transmit a first sensor signal based on the first movement;
   a second sensor configured to determine a second movement of the user manipulatable object in a second rotational degree of freedom and to transmit a second sensor signal based on the second movement;
   a third sensor configured to determine a third movement of the user manipulatable object in a third rotational degree of freedom and to transmit a third sensor signal based on the third movement;
   a fourth sensor configured to determine a fourth movement of the user manipulatable object in the translational degree of freedom and to transmit a fourth sensor signal based on the fourth movement; and
   a local processor in communication with the first, second, third, and fourth sensors and configured to:
   receive the first, second, third, and fourth sensor signals, and
   transmit a local processing signal to a host processor, the local processing signal based on at least one of the first, second, third, or fourth sensor signals.

2. The system of claim 1, further comprising:
   a first actuator configured to output a first force in the first rotational degree of freedom;
   a second actuator configured to output a second force in the second rotational degree of freedom;
   a third actuator configured to output a third force in the third rotational degree of freedom; and
   a fourth actuator configured to output a fourth force in the translational degree of freedom.

3. The system of claim 2, wherein the local processor is configured to output actuator signals to the first, second, third, and fourth actuators configured to cause the actuators to output the first, second, third, and fourth forces.

4. The system of claim 1, wherein the elongated member comprises a catheter.

5. The system of claim 1, wherein the laparoscopic handle comprises a grip configured to open and close about a pivot point, and wherein the system further comprises a fifth sensor to sense an open and close movement of the grip about the pivot point, the fifth sensor configured to transmit a fifth sensor signal based on the open and close movement.

6. The system of claim 5, further comprising an actuator configured to output a force about the pivot point.

7. The system of claim 5, wherein the local processing signal is based on at least one of the first, second, third, fourth, or fifth sensor signals, and further comprising the host processor in communication with the local processor, the host processor configured to:
   receive the local processing signal;
   execute a laparoscopic simulation; and
   display a simulated object in a simulated environment based on the local processing signal.

8. The system of claim 2, wherein the laparoscopic handle comprises a grip configured to open and close about a pivot point, and wherein the system further comprises a sensor to sense an open and close movement of the grip about the pivot point.

9. The system of claim 8, further comprising a fifth actuator configured to output a fifth force about the pivot point.

10. The system of claim 8 further comprising the host processor in communication with the local processor, the host processor configured to:
    receive the local processing signal;
    execute a laparoscopic simulation; and
    display a simulated object in a simulated environment based on the local processing signal.

11. A system comprising:
    a user manipulatable object comprising a tool handle and an elongated member extending from the tool handle;
    a gimbal mechanism coupled to the user manipulatable object, the gimbal mechanism configured to receive the elongated member of the user manipulatable object and to allow the user manipulatable object to move in at least three rotational degrees of freedom and a translational degree of freedom;
    a trocar coupled to the gimbal mechanism, the trocar configured to receive the elongated member of the user manipulatable object;
    a first sensor configured to determine a first movement of the user manipulatable object in a first rotational degree of freedom and to transmit a first sensor signal based on the first movement;
    a second sensor configured to determine a second movement of the user manipulatable object in a second rotational degree of freedom and to transmit a second sensor signal based on the second movement;
    a third sensor configured to determine a third movement of the user manipulatable object in a third rotational degree of freedom and to transmit a third sensor signal based on the third movement;
    a fourth sensor configured to determine a fourth movement of the user manipulatable object in the translational degree of freedom and to transmit a fourth sensor signal based on the fourth movement; and a local processor in communication with the first, second, third, and fourth sensors and configured to:
  receive the first, second, third, and fourth sensor signals, and
  transmit a local processing signal to a host processor, the local processing signal based on at least one of the first, second, third, or fourth sensor signals.

12. The system of claim 11, further comprising:
  a first actuator configured to output a first force in the first rotational degree of freedom;
  a second actuator configured to output a second force in the second rotational degree of freedom;
  a third actuator configured to output a third force in the third rotational degree of freedom; and
  a fourth actuator configured to output a fourth force in the translational degree of freedom.

13. The system of claim 12, wherein the local processor is configured to output actuator signals to the first, second, third, and fourth actuators configured to cause the actuators to output the first, second, third, and fourth forces.

14. The system of claim 11, wherein the elongated member comprises a catheter.

15. The system of claim 11, wherein the laparoscopic handle comprises a grip configured to open and close about a pivot point, and wherein the system further comprises a fifth sensor to sense an open and close movement of the grip about the pivot point, the fifth sensor configured to transmit a fifth sensor signal based on the open and close movement.

16. The system of claim 15, further comprising an actuator configured to output a force about the pivot point.

17. The system of claim 15, wherein the local processing signal is based on at least one of the first, second, third, fourth, or fifth sensor signals, and further comprising the host processor in communication with the local processor, the host processor configured to:
  receive the local processing signal;
  execute a laparoscopic simulation; and
  display a simulated object in a simulated environment based on the local processing signal.

18. The system of claim 12, wherein the laparoscopic handle comprises a grip configured to open and close about a pivot point, and wherein the system further comprises a sensor to sense an open and close movement of the grip about the pivot point.

19. The system of claim 18, further comprising a fifth actuator configured to output a fifth force about the pivot point.

20. The system of claim 18 further comprising the host processor in communication with the local processor, the host processor configured to:
  receive the local processing signal;
  execute a laparoscopic simulation; and
  display a simulated object in a simulated environment based on the local processing signal.

* * * * *